US012630507B2

(12) United States Patent
Jin et al.

(10) Patent No.: US 12,630,507 B2
(45) Date of Patent: May 19, 2026

(54) PYRROLIDINE AMIDE DERIVATIVE SALT AND USE THEREOF

(71) Applicant: SUNSHINE LAKE PHARMA CO., LTD., Guangdong (CN)

(72) Inventors: Chuanfei Jin, Dongguan (CN); Kangzhi Chen, Dongguan (CN); Yingjun Zhang, Dongguan (CN)

(73) Assignee: SUNSHINE LAKE PHARMA CO., LTD., Dongguan (CN)

(*) Notice: Subject to any disclaimer, the term of this patent is extended or adjusted under 35 U.S.C. 154(b) by 625 days.

(21) Appl. No.: 18/013,721

(22) PCT Filed: Jul. 6, 2021

(86) PCT No.: PCT/CN2021/104625
§ 371 (c)(1),
(2) Date: Dec. 29, 2022

(87) PCT Pub. No.: WO2022/007769
PCT Pub. Date: Jan. 13, 2022

(65) Prior Publication Data

US 2024/0317681 A1 Sep. 26, 2024

(30) Foreign Application Priority Data

Jul. 7, 2020 (CN) ......................... 202010643540.7

(51) Int. Cl.
*C07D 207/16* (2006.01)
*A61K 31/401* (2006.01)
*C07C 309/04* (2006.01)

(52) U.S. Cl.
CPC .......... *C07D 207/16* (2013.01); *A61K 31/401* (2013.01); *C07C 309/04* (2013.01); *C07B 2200/13* (2013.01)

(58) Field of Classification Search
CPC .. C07D 207/16; A61K 31/401; C07C 309/04; C07B 2200/13
See application file for complete search history.

(56) References Cited

U.S. PATENT DOCUMENTS

| | | | |
|---|---|---|---|
| 7,291,641 B2 | 11/2007 | Chabrier De Lassauniere et al. | |
| 11,225,460 B2 | 1/2022 | Jin et al. | |
| 2015/0274657 A1 | 10/2015 | Montagne et al. | |

FOREIGN PATENT DOCUMENTS

| | | | |
|---|---|---|---|
| CN | 113896670 A | 1/2022 | |
| CN | 113896671 A | 1/2022 | |
| CN | 113896672 A | 1/2022 | |
| CN | 110240557 B * | 5/2023 | .............. A61P 25/18 |
| WO | WO-2005040108 A1 * | 5/2005 | .............. A61P 25/00 |

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Patani et al. Chemical Reviews. 1996;96(8):3147-3176 (Year: 1996).*
Alborghetti et al. (Neural Regen Res. 2023;19(1): 16-21 (Year: 2023).*
Alsaad et al. (Molecules 2025, 30(1), 126) (Year: 2025).*
Gupta et al. (Molecules. 2018;23(7):1719 (Year: 2018).*
Oct. 13, 2021 International Search Report issued in International Patent Application No. PCT/CN2021/104625.
Oct. 13, 2021 Written Opinion issued in International Patent Application No. PCT/CN2021/104625.

* cited by examiner

*Primary Examiner* — Clinton A Brooks
*Assistant Examiner* — Jerica Katlynn Wilson
(74) *Attorney, Agent, or Firm* — Oliff PLC

(57) ABSTRACT

A pyrrolidine amide derivative salt and the use thereof. Further, a pharmaceutical composition containing the salt, and the use of the salt or the pharmaceutical composition containing the salt in the preparation of a drug for preventing, treating or alleviating diseases adjusted by means of MAO-B, wherein the diseases include neurodegenerative diseases, in particular Parkinson's disease.

10 Claims, 13 Drawing Sheets

PYRROLIDINE AMIDE DERIVATIVE SALT AND USE THEREOF

CROSS-REFERENCE TO RELATED APPLICATION

This application claims the priority and benefits of Chinese Patent Application No. 202010643540.7, filed with the State Intellectual Property Office of China on Jul. 7, 2020, which is incorporated herein by reference in its entirety.

FIELD OF THE INVENTION

The invention belongs to the technical field of medicine, and relates to salts of pyrrolidine amide derivatives and uses thereof. It specifically relates to the salt of (2S,4S)-4-fluoro-1-(4-(3-fluorobenzyloxy)benzyl)pyrrolidine-2-carboxamide, the crystal form of the salt and their uses, and further relates to a pharmaceutical composition comprising the salt or the crystal form of the salt.

BACKGROUND ART

Parkinson's disease (Parkinson's disease, PD) is a common chronic degenerative disease of the nervous system. It is more common in the elderly, with an average age of onset of around 60 years old, and young Parkinson's disease with onset under the age of 40 is rare. The prevalence of PD among people over 65 years old in China is about 1.7%. Most patients with Parkinson's disease are sporadic cases, and less than 10% of patients have a family history. Parkinson's disease has an insidious onset and slow progression. The first symptom is usually tremor or clumsiness in one extremity, which then involves the opposite extremity. Clinically, the main manifestations are resting tremor, bradykinesia, muscle rigidity, and posture and gait disturbance. In recent years, more and more people have noticed that non-motor symptoms such as depression, constipation and sleep disturbance are also common complaints of patients with Parkinson's disease, and their impact on the quality of life of patients even exceeds that of motor symptoms.

The main pathological change of Parkinson's disease is the degeneration and death of dopaminergic (dopamine, DA) neurons in the substantia nigra of the midbrain, which leads to a significant decrease in the content of DA in the striatum and causes the disease. The exact cause of this pathological change is still unclear. Genetic factors, environmental factors, aging, oxidative stress, etc. may all be involved in the degeneration and death process of PD dopaminergic neurons.

The incidence of most cases is likely to be related to environmental factors, or the result of the interaction between environmental factors and genetic factors. Part of the pathogenesis involves free radicals, oxidative stress, glutamate excitotoxicity, lack of neurotrophic agents, inflammation, apoptosis, and loss of mitochondrial complex I, which interact in a cascade of biochemical reactions culminating in neuronal death (Teismann P, Schulz J B. Cellular pathology of Parkinson's disease: astrocytes, microglia and inflammation [J]. Cell Tissue Res, 2004, 318: 149-161). Genetic factors play a decisive role in some familial PD. Recent genetic studies have found that in the pathogenesis of most PDs, functional defects in the ubiquitin-proteasome system and abnormal aggregation of denatured proteins play an important role. In addition, factors such as oxidative stress and the formation of free radicals, excitotoxicity mediated by excessive glutamate release, mitochondrial dysfunction, inflammation, and neuronal apoptosis caused by damage to the ubiquitin-proteasome system are closely related to the progression of the disease.

Currently, the main treatment for PD is the symptomatic treatment of dopamine replacement, and levodopa (L-dopa) is still the most effective drug to control the symptoms and signs of PD clinically (RASCO O, GOETZ C, KOLLER W, et al. Treatment interventions for Parkinson's disease: an evidence based assessment [J]. Lancet, 2002, 359 (9317): 1589-1598). Although L-dopa can temporarily control the symptoms of PD, long-term use can cause many adverse reactions such as dyskinesias, motor fluctuations, and psychiatric symptoms. Although the use of continuous stimulation of dopaminergic neurons, surgical deep brain stimulation (deep brain stimulation, DBS), long-acting dopamine receptor agonists can reduce the occurrence of these complications to some extent (SCHAPIRA A H V, EMREB M, JENNER P, et al. Levodopa in the treatment of Parkinson's disease [J]. Eur J Neurol, 2009, 16 (9): 982-989), but it cannot delay the progression of the disease. In addition, dopamine receptor agonists such as cabergoline, catechol-oxo-methyltransferase (COMT) inhibitors such as entacapone (Comtan), glutamate receptor antagonists such as memantine, and anticholinergic preparations such as benzhexol (Antan) all have adverse reactions, but they can all be used as adjuvant drugs for levodopa, and can enhance the efficacy of levodopa through different mechanisms of combined drugs, reduce the dosage of levodopa and reduce adverse reactions. Therefore, it is particularly important to research and develop new drugs that can not only improve the symptoms of DA-ergic and non-DA-ergic systems in PD patients, but also slow down or even prevent the progression of the disease and exert neuroprotective effects.

Monoamine oxidase (MAO, EC 1.4.3.4) is a flavin-containing enzyme that catalyzes the oxidative deamination reaction of monoamine, responsible for oxidative deamination of endogenous monoamine neurotransmitters. Endogenous monoamine neurotransmitters include: dopamine, serotonin, epinephrine or norepinephrine, and trace amines such as phenylethylamine as well as many amine xenobiotics. Monoamine oxidase can be divided into two subtypes, monoamine oxidase A (MAO-A) and monoamine oxidase B (MAO-B). They are genetically encoded differently (A. W. Bach et al., Proc. Natl. Acad. Sci. USA 1988, 85, 4934-4938) and also differ in structure, tissue distribution and substrate specificity. MAO-A mostly exists in the liver and gastrointestinal mucosa, which can inactivate catecholamines in the blood circulation system and vasoactive substances (such as tyrosine) in the diet, thereby assisting the degradation of neurotransmitters in the brain; while MAO-B mainly exists in the brain and platelets. MAO-A has a higher affinity for octopamine, serotonin, epinephrine and norepinephrine; while the natural substrates of MAO-B are tyramine and phenylethylamine. However, both isoforms can oxidize dopamine.

Monoamine oxidase B (MAO-B) is one of the key enzymes of DA catabolism, by selectively and specifically inhibiting the decomposition of endogenous and exogenous dopamine, prolonging the action time of dopamine, thereby improving clinical symptoms. It can be used for early monotherapy of PD and adjuvant therapy after symptom fluctuation. It mainly has the following three functions: (1) decomposes dopamine into 3,4-dihydroxyphenylacetic acid and homovanillic acid, and produces small molecule $H_2O_2$ at the same time, which has a toxic effect on nerve cells: (2) deaminates and inactivates β-phenethylamine that stimulates dopamine secretion and inhibits dopamine reuptake;

(3) can also decompose 1-methyl-4-phenyl-1,2,3,6-tetrahydropyrimidine (MPTP) into neurotoxic 1-methyl-4-phenylpyridinium ion ($MPP^+$). Therefore, according to the physiological function of MAO-B, on the one hand, inhibiting the activity of MAO-B can reduce the degradation and reuptake of dopamine, increase the concentration of dopamine in the brain, and improve the clinical symptoms of PD; on the other hand, delaying the death process of substantia nigra cells by reducing the levels of neurotoxins such as $H_2O_2$ and $MPP^+$ (HEIKKILA R E, MANZINO L, CABBAT F S, et al. Protection against the dopaminergic neurotoxicity of 1-methyl-1,2,3,6-tetrahydropyridine (MPTP) by monoamine inhibitors [P]. Nature, 1984, 311 (5985): 467-469; YOUDIM M B H, BAKHLE Y S. Monoamine oxidase isoforms and inhibitors in Parkinson's disease and depressive illness [J]. Br J Pharmacol, 2006, 147 (S1): S287-5296; NAOI M, WAKAKO M. Monoamine oxidase inhibitors as neuroprotective agents in age-dependent neurodegenerative disorders [J]. Curr Pharm Des, 2010, 16 (25): 2799-2817) can change the progression of PD. Because MAO-B inhibitors can not only improve the symptoms of PD, but also play a neuroprotective role, they are currently a hot spot in the research of anti-Parkinson's disease drugs.

International application WO 2019170115 A1 discloses the compound (2S,4S)-4-fluoro-1-(4-(3-fluorobenzyloxy) benzyl)pyrrolidine-2-carboxamide (compound having formula (I)), which has a good inhibitory effect on the activity of MAO-B. However, there is no research on the salt of this compound or its crystal form in the prior art.

(I)

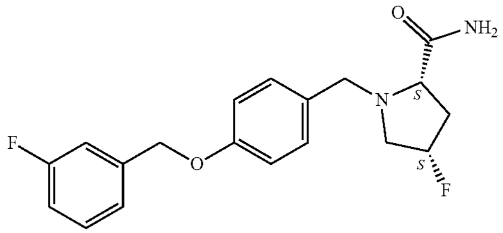

Different salts and solid forms of pharmaceutically active ingredients may have different properties. Different salts and solid forms may have significant differences in appearance, solubility, melting point, dissolution, bioavailability, etc., and may have different effects on the stability, bioavailability and efficacy of the drug. Therefore, the salt form and/or solid form of the drug should be fully considered in drug research and development.

When the inventors were studying the compound, they found that the compound has poor water solubility and poor druggability. Therefore, in order to find a solid form with better druggability, through a large number of experimental studies, it was found that after the compound having formula (I) forms a salt, the physicochemical properties of different salts change greatly, and the properties of some salts are not better than those of the free state of the compound: the inventors found that the physical properties and various properties of the mesylate of the compound having formula (I) prepared according to the method of the present invention can be significantly improved, which is more conducive to the development of preparations.

SUMMARY

The present invention provides a salt of the compound having formula (I), and the preparation of the salt, the solid form of the salt, its physicochemical properties and pharmacological properties have been studied, and it is found that the salts formed by the compound and different acids have relatively different physicochemical properties; among them, the various physical and chemical properties of mesylate are better than other salts, for example, the mesylate crystal form B obtained after the compound having formula (I) forms a salt with methanesulfonic acid has better pharmacokinetic properties than the corresponding hydrochloride crystal form A, maleate crystal form A, and p-toluenesulfonate crystal form A. Therefore, the mesylate crystal form B of the present invention has better properties, better pharmacokinetic properties, and thus better druggability.

Specifically, the present invention relates to a salt of a compound having formula (I), and use of a crystal form of the salt or a pharmaceutical composition comprising the salt or a crystal form of the salt in the manufacture of a medicament for preventing, treating or alleviating diseases regulated by MAO-B, including neurodegenerative diseases, especially Parkinson's disease. The salt described in the present invention is mesylate. Further, the salt described in the present invention is mesylate crystal form B. The crystal forms of the present invention may also be in the form of solvates, such as hydrates.

In one aspect, the present invention provides a salt of the compound having formula (I), (I)

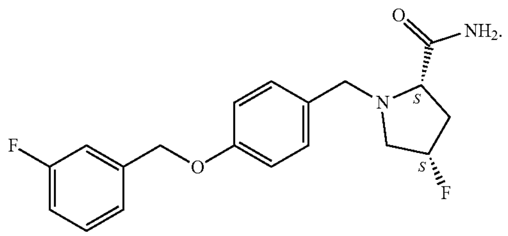

In some embodiments, the salts described herein are salts of organic or inorganic acids.

In other embodiments, the inorganic acid salts described in the present invention include, but are not limited to, hydrochloride, hydrobromide, phosphate, nitrate or sulfate, etc.; the organic acid salts include, but are not limited to, acetate, oxalate, fumarate, maleate, tartrate, citrate, succinate, camphorsulfonate, malonate, benzoate, salicylate, benzenesulfonate, mesylate or p-toluenesulfonate, etc.

In some embodiments, the salt of the compound having formula (I) of the present invention is mesylate.

In some embodiments, the salt described in the present invention is mesylate, and the mesylate is mesylate crystal form B. The X-ray powder diffraction pattern of the mesylate crystal form B comprises peaks expressed as 2θ at: 4.19°±0.20, 12.52°±0.20, 16.72°±0.20, 17.60°±0.2°, 20.190°±0.2°, 21.080±0.2°.

In some embodiments, the salt described in the present invention is mesylate, and the mesylate is mesylate crystal form B. The X-ray powder diffraction pattern of the mesylate crystal form B comprises peaks expressed as 2θ at: 4.190°±0.2°, 8.33°±0.2°, 12.52°±0.2°, 16.72°±0.2°, 17.600°±0.2°, 20.19°±0.2°, 21.08°±0.20, 22.35°±0.2°, 25.22°±0.20, 29.50°±0.20, 33.85°±0.20.

In some embodiments, the salt described in the present invention is mesylate, and the mesylate is mesylate crystal form B. The mesylate crystal form B has an X-ray powder diffraction pattern substantially as shown in FIG. 2.

In some embodiments, the salt described in the present invention is mesylate, and the mesylate is mesylate crystal form B. The differential scanning calorimetry diagram of the mesylate crystal form B comprises an endothermic peak at 230.55° C.±3° C.

In some embodiments, the salt described in the present invention is mesylate, and the mesylate is mesylate crystal form B. The mesylate crystal form B has a differential scanning calorimetry diagram substantially as shown in FIG. 12.

In some embodiments, the salt described in the present invention is mesylate, and the mesylate is mesylate crystal form A. The X-ray powder diffraction pattern of the mesylate crystal form A comprises peaks expressed as 2θ at: 11.79°±0.2°, 13.11°±0.2°, 17.46°±0.2°, 17.55°±0.2°, 17.81°±0.2°, 18.37°±0.2°, 19.85°±0.2°, 21.43°±0.2°, 21.65°±0.2°, 22.28°±0.2°.

In some embodiments, the salt described in the present invention is mesylate, and the mesylate is mesylate crystal form A. The X-ray powder diffraction pattern of the mesylate crystal form A comprises peaks expressed as 2θ at: 4.38°±0.2°, 1.79°±0.2°, 13.11°±0.2°, 17.46°±0.2°, 17.55°±0.2°, 17.81°±0.2°, 18.37°±0.2°, 19.85°±0.2°, 21.43°±0.2°, 21.65°±0.2°, 22.28°±0.2°, 26.14°±0.2°, 28.92°±0.2°.

In some embodiments, the salt described in the present invention is mesylate, and the mesylate is mesylate crystal form A. The X-ray powder diffraction pattern of the mesylate crystal form A comprises peaks expressed as 2θ at: 4.38°±0.2°, 11.79°±0.2°, 13.11°±0.2°, 16.63°±0.2°, 16.95°±0.2°, 17.46°±0.2°, 17.55°±0.2°, 17.810°±0.2°, 18.37°±0.2°, 19.210°±0.2°, 19.85°±0.2°, 20.65°±0.2°, 20.87°±0.2°, 21.43°±0.2°, 21.65°±0.2°, 22.28°±0.2°, 22.95°±0.2°, 24.92°±0.2°, 25.74°±0.2°. 26.14°±0.2°, 26.86°±0.2°, 28.42°±0.2°. 28.92°±0.2°, 29.28°±0.2°, 29.95°±0.2°, 30.94°±0.20, 32.09°±0.2°, 35.49°±0.2°.

In some embodiments, the salt described in the present invention is mesylate, and the mesylate is mesylate crystal form A. The mesylate crystal form A has an X-ray powder diffraction pattern substantially as shown in FIG. 1.

In some embodiments, the salt described in the present invention is mesylate, and the mesylate is mesylate crystal form A. The differential scanning calorimetry diagram of the mesylate crystal form A comprises an endothermic peak at 238.12° C.±3° C.

In some embodiments, the salt described in the present invention is mesylate, and the mesylate is mesylate crystal form A. The mesylate crystal form A has a differential scanning calorimetry diagram substantially as shown in FIG. 11.

In some embodiments, the salt described in the present invention is mesylate, and the mesylate is mesylate crystal form C. The X-ray powder diffraction pattern of the mesylate crystal form C comprises peaks expressed as 2θ at: 4.22°±0.2°, 12.56°±0.2°, 16.77°±0.2°, 18.27°±0.2°, 19.44°±0.2°, 20.25°±0.2°, 21.18°±0.2°.

In some embodiments, the salt described in the present invention is mesylate, and the mesylate is mesylate crystal form C. The X-ray powder diffraction pattern of the mesylate crystal form C comprises peaks expressed as 2θ at: 4.22°±0.2°, 12.56°±0.2°, 16.77°±0.2°, 17.66°±0.2°, 17.84°±0.2°. 18.27°±0.2°. 18.82°±0.2°, 19.44°±0.2°, 20.25°±0.2°, 21.18°±0.2°, 22.88°±0.2°, 23.11°±0.2°, 26.13°±0.2°, 33.88°±0.2°.

In some embodiments, the salt described in the present invention is mesylate, and the mesylate is mesylate crystal form C. The mesylate crystal form C has an X-ray powder diffraction pattern substantially as shown in FIG. 3.

In some embodiments, the salt described in the present invention is mesylate, and the mesylate is mesylate crystal form D. The X-ray powder diffraction pattern of the mesylate crystal form D comprises peaks expressed as 2θ at: 4.32°±0.2°, 8.58°±0.2°, 9.59°±0.2°, 12.12°±0.2°, 13.54°±0.2°, 16.33°±0.2°, 18.47°±0.2°, 19.21°±0.2°, 20.37°±0.2°.

In some embodiments, the salt described in the present invention is mesylate, and the mesylate is mesylate crystal form D. The X-ray powder diffraction pattern of the mesylate crystal form D comprises peaks expressed as 2θ at: 4.32°±0.2°, 8.58°±0.2°, 9.59°±0.2°, 12.12°±0.2°, 13.54°±0.2°, 15.41°±0.2°, 16.33°±0.2°, 17.70°±0.2°, 18.47°±0.2°, 19.21°±0.2°, 20.37°±0.2°, 21.48°±0.2°, 21.99°±0.2°, 23.19°±0.2°, 23.76°±0.2°, 24.57°±0.2°, 25.110°±0.2°, 25.94°±0.2°, 27.29°±0.2°, 28.89°±0.2°.

In some embodiments, the salt described in the present invention is mesylate, and the mesylate is mesylate crystal form D. The mesylate crystal form D has an X-ray powder diffraction pattern substantially as shown in FIG. 4.

In some embodiments, the salt described in the present invention is mesylate, and the mesylate is mesylate crystal form E. The X-ray powder diffraction pattern of the mesylate crystal form E comprises peaks expressed as 2θ at: 4.29°±0.2°, 8.52°±0.2°, 9.53°±0.2°, 12.07°±0.2°, 13.50°±0.2°, 16.27°±0.2°, 17.63°±0.2°, 18.40°±0.2°, 19.14°±0.2°, 20.31°±0.2°.

In some embodiments, the salt described in the present invention is mesylate, and the mesylate is mesylate crystal form E. The X-ray powder diffraction pattern of the mesylate crystal form E comprises peaks expressed as 2θ at: 4.29°±0.2°, 8.52°±0.2°, 9.53°±0.2°, 12.07°±0.2°, 12.80°±0.2°, 13.50°±0.2°, 15.13°±0.2°, 15.41°±0.2°, 16.27°±0.2°, 17.63°±0.2°, 18.40°±0.2°, 19.14°±0.2°, 20.31°±0.2°, 21.42°±0.2°, 21.86°±0.2°, 24.48°±0.2°, 26.14°±0.2°, 27.54°±0.2°, 28.06°±0.2°, 28.79°±0.2°, 34.89°±0.2°.

In some embodiments, the salt described in the present invention is mesylate, and the mesylate is mesylate crystal form E. The mesylate crystal form E has an X-ray powder diffraction pattern substantially as shown in FIG. 5.

In some embodiments, the salt described in the present invention is mesylate, and the mesylate is mesylate crystal form E. The differential scanning calorimetry diagram of the mesylate crystal form E comprises an endothermic peak at 238.07° C.±3° C.

In some embodiments, the salt described in the present invention is mesylate, and the mesylate is mesylate crystal form E. The mesylate crystal form E has a differential scanning calorimetry diagram substantially as shown in FIG. 13.

In some embodiments, the salt described in the present invention is mesylate, and the mesylate is mesylate crystal form F. The X-ray powder diffraction pattern of the mesylate crystal form F comprises peaks expressed as 2θ at: 10.92°±0.2°, 13.13°±0.2°, 17.53°±0.2°, 17.82°±0.2°, 18.38°±0.2°, 19.19°±0.2°, 19.86°±0.2°, 21.41°±0.2°, 22.27°±0.2°.

In some embodiments, the salt described in the present invention is mesylate, and the mesylate is mesylate crystal form F. The X-ray powder diffraction pattern of the mesylate crystal form F comprises peaks expressed as 2θ at: 4.40°±0.2°, 10.92°±0.2°, 11.77°±0.2°, 13.13°±0.2°, 16.74°±0.2°. 17.53°±0.2°, 17.82°±0.2°, 18.38°±0.2°, 19.19°±0.2°. 19.86°±0.2°, 20.86°±0.2°, 21.41°±0.2°, 22.27°±0.2°, 23.00°±0.2°, 25.75°±0.2°, 28.94°±0.2°. 29.96°±0.2°. 30.93°±0.2°.

In some embodiments, the salt described in the present invention is mesylate, and the mesylate is mesylate crystal form F. The mesylate crystal form F has an X-ray powder diffraction pattern substantially as shown in FIG. 6.

In some embodiments, the salt described in the present invention is mesylate, and the mesylate is mesylate crystal form G The X-ray powder diffraction pattern of the mesylate crystal form G comprises peaks expressed as 2θ at: 6.65°±0.2°, 7.16°±0.2°. 8.78°±0.2°, 11.59°±0.2°. 12.96°±0.2°, 13.13°±0.2°, 14.36°±0.2°, 17.37°±0.2°, 17.64°±0.2°, 19.74°±0.2°, 20.54°±0.2°.

In some embodiments, the salt described in the present invention is mesylate, and the mesylate is mesylate crystal form G The X-ray powder diffraction pattern of the mesylate crystal form G comprises peaks expressed as 2θ at: 6.65°±0.2°, 7.16°±0.2°, 8.78°±0.2°, 9.01°±0.2°, 10.17°±0.2°, 11.59°±0.2°, 12.12°±0.2°, 12.96°±0.2°, 13.13°±0.2°, 14.36°±0.2°, 15.93°±0.2°, 17.37°±0.2°, 17.64°±0.2°, 18.36°±0.2°, 18.68°±0.2°, 19.19°±0.2°, 19.74°±0.2°, 20.54°±0.2°, 21.41°±0.2°. 22.18°±0.2°, 23.01°±0.2°, 26.14°±0.2°.

In some embodiments, the salt described in the present invention is mesylate, and the mesylate is mesylate crystal form G. The mesylate crystal form G has an X-ray powder diffraction pattern substantially as shown in FIG. 7.

In some embodiments, the salt described in the present invention is hydrochloride, and the hydrochloride is hydrochloride crystal form A. The X-ray powder diffraction pattern of the hydrochloride crystal form A comprises peaks expressed as 2θ at: 7.54°±0.2°, 12.49°±0.2°, 15.16°±0.2°, 16.49°±0.2°, 18.32°±0.2°, 19.34°±0.2°, 19.92°±0.2°, 22.50°±0.2°.

In some embodiments, the salt described in the present invention is hydrochloride, and the hydrochloride is hydrochloride crystal form A. The X-ray powder diffraction pattern of the hydrochloride crystal form A comprises peaks expressed as 2θ at: 7.05°±0.2°, 7.54°±0.2°, 12.49°±0.2°, 14.13°±0.2°, 15.16°±0.2°, 16.49°±0.2°, 18.32°±0.2°, 19.34°±±0.2°, 19.92°±0.2°, 21.28°±0.2°, 22.50°±0.2°, 23.63°±0.2°, 25.40°±0.2°, 25.86°±0.2°, 26.93°±0.2°, 27.42°±0.2°, 27.92°±0.2°, 29.21°±0.2°, 29.38°±0.2°, 35.14°±0.2°.

In some embodiments, the salt described in the present invention is hydrochloride, and the hydrochloride is hydrochloride crystal form A. The hydrochloride crystal form A has an X-ray powder diffraction pattern substantially as shown in FIG. 8.

In some embodiments, the salt described in the present invention is hydrochloride, and the hydrochloride is hydrochloride crystal form A. The differential scanning calorimetry diagram of the hydrochloride crystal form A comprises an endothermic peak at 264.34° C. f 3° C.

In some embodiments, the salt described in the present invention is hydrochloride, and the hydrochloride is hydrochloride crystal form A. The hydrochloride crystal form A has a differential scanning calorimetry diagram substantially as shown in FIG. 14.

In some embodiments, the salt described in the present invention is maleate, and the maleate is maleate crystal form A. The X-ray powder diffraction pattern of the maleate crystal form A comprises peaks expressed as 2θ at: 6.25°±0.2, 9.37°±0.2°, 9.66°±0.2°, 15.08°±0.2°. 16.60°±0.2°, 18.93°±0.2°, 21.06°±0.20, 22.95°±0.20, 27.99°±0.2°.

In some embodiments, the salt described in the present invention is maleate, and the maleate is maleate crystal form A. The X-ray powder diffraction pattern of the maleate crystal form A comprises peaks expressed as 2θ at: 6.25°±0.2°, 9.37°±0.2°, 9.66°±0.2°, 15.08°±0.2°, 16.60°±0.2°, 17.74°±0.2°, 18.41°±0.2°, 18.93°±0.2°, 20.54°±0.2°, 21.06°±0.2°, 21.79°±0.2°, 22.95°±0.2°, 24.72°±0.2°, 25.38°±0.2°, 27.28°±0.2°, 27.99°±0.2°, 29.40°±0.2°, 30.07°±0.2°, 31.85°±0.2°, 33.73°±0.2°, 34.64°±0.2°.

In some embodiments, the salt described in the present invention is maleate, and the maleate is maleate crystal form A. The maleate crystal form A has an X-ray powder diffraction pattern substantially as shown in FIG. 9.

In some embodiments, the salt described in the present invention is maleate, and the maleate is maleate crystal form A. The differential scanning calorimetry diagram of the maleate crystal form A comprises an endothermic peak at 218.14° C.±3° C.

In some embodiments, the salt described in the present invention is maleate, and the maleate is maleate crystal form A. The maleate crystal form A has a differential scanning calorimetry diagram substantially as shown in FIG. 15.

In some embodiments, the salt described in the present invention is p-toluenesulfonate, and the p-toluenesulfonate is p-toluenesulfonate crystal form A. The X-ray powder diffraction pattern of the p-toluenesulfonate crystal form A comprises peaks expressed as 2θ at: 4.25°±0.2°, 8.44°±0.2°, 9.35°±0.2°, 9.59°±0.2°, 13.26°±0.2°, 13.55°±0.2°, 15.10°±0.2°, 15.49°±0.2°, 17.75°±0.2°, 18.24°±0.2°, 18.85°±0.2°, 19.17°±0.2°, 25.75°±0.2°, 25.96°±0.2°.

In some embodiments, the salt described in the present invention is p-toluenesulfonate, and the p-toluenesulfonate is p-toluenesulfonate crystal form A. The X-ray powder diffraction pattern of the p-toluenesulfonate crystal form A comprises peaks expressed as 2θ at: 4.25°±0.2°, 8.44°±0 0.2°, 9.35°±0.2°, 9.59°±0.2°, 13.26°±0.2°, 13.55°±0.2°, 15.10°±0.2°, 15.49°±0.2°, 17.75°±0.2°. 18.24°±0.2°, 18.85°±0.2°, 19.17°±0.2°, 21.00°±0.2°, 21.15°±0.2°, 25.75°±0.2°, 25.96°±0.2°.

In some embodiments, the salt described in the present invention is p-toluenesulfonate, and the p-toluenesulfonate is p-toluenesulfonate crystal form A. The X-ray powder diffraction pattern of the p-toluenesulfonate crystal form A comprises peaks expressed as 2θ at: 4.25°±0.2°, 8.44°±0.2°, 9.35°±0.2°, 9.59°±0.2°, 11.84°±0.2°, 13.26°±0.2°, 13.55°±0.2°, 15.10°±0.2°, 15.49°±0.2°, 16.63°±0.2°, 17.75°±0.2°, 18.24°±0.2°, 18.85°±0.2°, 19.17°±0.2°, 19.59°±0.2°, 21.00°±0.2°, 21.15°±0.2°, 21.43°±0.2°, 22.83°±0.2°, 23.20°±0.2°, 24.63°±0.2°, 25.46°±0.2°, 25.75°±0.2°, 25.96°±0.2°, 28.31°±0.2°, 29.06°±0.2°, 30.34°±0.2°.

In some embodiments, the salt described in the present invention is p-toluenesulfonate, and the p-toluenesulfonate is p-toluenesulfonate crystal form A. The p-toluenesulfonate crystal form A has an X-ray powder diffraction pattern substantially as shown in FIG. 10.

In some embodiments, the salt described in the present invention is p-toluenesulfonate, and the p-toluenesulfonate is p-toluenesulfonate crystal form A. The differential scanning calorimetry diagram of the p-toluenesulfonate crystal form A comprises endothermic peaks at 130.74° C. f 3° C. and 242.83° C. f 3° C.

In some embodiments, the salt described in the present invention is p-toluenesulfonate, and the p-toluenesulfonate is p-toluenesulfonate crystal form A. The p-toluenesulfonate crystal form A has a differential scanning calorimetry diagram substantially as shown in FIG. 16.

In another aspect, the present invention relates to a pharmaceutical composition comprising any one of the salts described in the present invention, and a pharmaceutically acceptable carrier, excipient, diluent, adjuvant or a combination thereof.

In one aspect, the present invention relates to use of the salt or the pharmaceutical composition in the manufacture of a medicament for preventing, treating or alleviating diseases regulated by MAO-B in a subject.

In one aspect, the present invention relates to the salt or the pharmaceutical composition for use in preventing, treating or alleviating diseases regulated by MAO-B in a subject.

In one aspect, the present invention relates to a method of preventing, treating or alleviating diseases regulated by MAO-B in a subject, comprising administering to the subject a therapeutically effective amount of the salt or the pharmaceutical composition.

In some embodiments, the disease regulated by MAO-B of the invention is a neurodegenerative disease, psychosis or cancer.

In some embodiments, the neurodegenerative disease of the invention is Parkinson's disease, cerebral ischemia. Alzheimer's disease, amyotrophic lateral sclerosis, bovine spongiform encephalopathy, Huntington's disease, Creutzfeldt-Jakob disease, ataxia-telangiectasia, cerebellar atrophy, spinal muscular atrophy, primary lateral sclerosis, or multiple sclerosis.

In another aspect, the present invention relates to use of the salt or the pharmaceutical composition in the preparation of a medicament for inhibiting MAO-B.

In another aspect, the present invention relates to the salt or the pharmaceutical composition for use in inhibiting MAO-B.

In another aspect, the present invention relates to a method of inhibiting MAO-B in a subject, comprising administering to the subject a therapeutically effective amount of the salt or the pharmaceutical composition.

In another aspect, the present invention also relates to a method for preparing a salt of a compound having formula (I) or a crystal form thereof.

The solvent used in the preparation method of the salt or its crystal form in the present invention is not particularly restricted, and any solvent which dissolves the starting material to a degree and does not affect its properties is contained in the present invention. Additionally, many similar modifications in the art, equivalent replacements, or solvent, solvent composition and the solvent composition with different proportions which are equivalent to those described in the invention, all are deemed to be included in the present invention. The present invention gives the preferred solvent for each reaction step.

The preparation of the salt or its crystal form of the present invention will be described in detail in the examples section. At the same time, the present invention provides a pharmacological property testing experiment (such as a pharmacokinetic experiment), a solubility experiment, a stability experiment, and a hygroscopicity experiment of the salt or its crystal form. Experiments have proved that the mesylate crystal form B of the present invention has unexpected technical advantages:

1. The mesylate crystal form B has good stability, for example, it has no or almost no hygroscopicity, it will not change when placed at room temperature, and it is also very stable under high temperature, high humidity and light conditions, the appearance and purity are basically unchanged; the water solubility is good.
2. Compared with other salts, such as hydrochloride crystal form A, maleate crystal form A, and p-toluenesulfonate crystal form A, the mesylate crystal form B has higher blood drug concentration and exposure in rats, thus having better pharmacokinetic properties.

Therefore, the mesylate crystal form B of the present invention has better biological activity and higher stability, and is more suitable for pharmaceutical use.

Definitions and General Terminology

Unless otherwise indicated, all technical and scientific terms used in the present invention have the same meaning as commonly understood by one of ordinary skill in the art to which this invention pertains. All patents and publications referred to herein are incorporated by reference in their entirety. Although any methods and materials similar or identical to those described herein may be used in the practice or testing of the invention, but the methods, apparatus and materials described in the invention are preferred.

"Crystal form" or "crystalline form" refers to a solid having a highly regular chemical structure, including, but not limiting to, mono- or multi-component crystals, and/or polymorphs of compounds, solvates, hydrates, clathrates, eutectic, salt, solvates of salt, hydrates of salt. The crystalline form of the material can be obtained by a number of methods known in the field. Such methods include, but are not limited to, melt crystallization, melt cooling, solvent crystallization, crystallization in defined space, for example, in nanopores or capillaries, on a surface or template, for example, on a polymer, in the presence of additives such as co-crystallized antimolecules, removing solvent, dehydration, rapid evaporation, rapid cooling, slow cooling, vapor diffusion, sublimation, reaction crystallization, anti-solvent addition, grinding and solvent drop milling, and the like.

"amorphous" or "amorphous form" refers to a substance formed when the mass point (molecule, atom, ion) of a substance is arranged in a non-periodic manner in a three-dimensional space, characterized by an X-ray powder diffraction pattern with diffuse undisturbed peaks. Amorphous form is a special physical form of solid matter, its local and orderly structural features suggest that it is inextricably linked with the crystalline material. The amorphous form of the material can be obtained by a number of methods known in the field. Such methods include, but are not limited to, quenching, anti-solvent flocculation, ball milling, spray drying, freeze drying, wet granulation and solid dispersion techniques.

"Solvent" refers to a substance (typically a liquid) that is capable of completely or partially dissolving another substance (typically a solid). Solvents for use in the practice of this invention include, but are not limited to, water, acetic acid, acetone, acetonitrile, benzene, chloroform, carbon tetrachloride, dichloromethane, dimethylsulfoxide, 1,4-dioxane, ethanol, ethyl acetate, dimethyl carbonate, butanol, t-butanol, N N-dimethylacetamide, N, N-dimethylformamide, formamide, formic acid, heptane, hexane, isopropanol, methanol, methyl ethyl ketone, mesitylene, nitromethane, polyethylene glycol, propanol, pyridine, tetrahydrofuran, toluene, xylene, mixtures thereof, and the like.

"Anti-solvent" refers to a fluid that promotes the precipitation of a product (or product precursor) from a solvent. The anti-solvent may comprise a cold gas, or a fluid that promotes the precipitation of the fluid by chemical reaction or reduces the solubility of the product in the solvent; it may be the same liquid as the solvent but at a different temperature, or it may be a liquid different from the solvent.

"Solvate" refers to a compound having a solvent on a surface, in a lattice or both on a surface or in a lattice. The solvent can be water, acetic acid, acetone, acetonitrile, benzene, chloroform, carbon tetrachloride, dichloromethane, dimethylsulfoxide, 1,4-dioxane, ethanol, ethyl acetate, dimethyl carbonate, butanol, t-butanol, N, N-dimethylacetamide, N, N-dimethylformamide, formamide, formic acid, heptane, hexane, isopropanol, methanol, methyl ethyl ketone, methyl pyrrolidone, mesitylene, nitromethane, polyethylene glycol, propanol, pyridine, tetrahydrofuran, toluene, xylene, mixtures thereof, and the like. A specific example of the solvate is a hydrate in which the solvent on the surface, in the lattice or on the surface and in the lattice is water. On the surface, in the lattice or on the surface and in the lattice of the substance, the hydrate may or may not have any solvent other than water.

Crystal form can be identified by a variety of technical means, such as X-ray powder diffraction (XRPD), infrared absorption spectroscopy (IR), melting point method, differential scanning calorimetry (DSC), thermogravimetric analysis (TGA), Nuclear magnetic resonance. Raman spectroscopy. X-ray single crystal diffraction, dissolution calorimetry, scanning electron microscopy (SEM), quantitative analysis, solubility and dissolution rate.

X-ray powder diffraction (XRPD) can detect changes in crystal form, crystallinity, crystal state and other information, is a common means for identifying crystal form. The peak position of the XRPD pattern primarily depends on the structure of the crystal form and is relatively insensitive to the experimental details, and its relative peak height depends on many factors associated with sample preparation and instrument geometry. Thus, in some embodiments, the crystalline form of the present invention is characterized by an XRPD pattern having certain peak positions, which is substantially as shown in the XRPD pattern provided in the drawings of the present invention. At the same time, the 2θ of the XRPD pattern can be measured with an experimental error. The measurement of 2θ of the XRPD pattern may be slightly different between the different instruments and the different samples. Therefore, the value of 2θ cannot be regarded as absolute. According to the condition of the instrument used in this test, the diffraction peak has an error tolerance of ±0.2°.

Differential Scanning Calorimetry (DSC) is a technique of measuring the energy difference between a sample and an inert reference (commonly used $\alpha$-$Al_2O_3$) with temperature by continuously heating or cooling under program control. The endothermic peak height of the DSC diagram depends on many factors associated with sample preparation and instrument geometry, while the peak position is relatively insensitive to experimental details. Thus, in some embodiments, the crystal form of the present invention is characterized by a DSC diagram having certain peak positions, which is substantially as shown in the DSC diagram provided in the drawings of the present invention. At the same time, the DSC diagram can be measured with an experimental error. The peak position and peak value of DSC diagram may be slightly different between the different instruments and the different samples. Therefore, the peak position or the peak value of the DSC endothermic peak cannot be regarded as absolute. According to the condition of the instrument used in this test, the endothermic peak has an error tolerance of ±3° C.

Thermogravimetric analysis (TGA) is a technique for measuring the quality of a substance with temperature under the control of a program. It is suitable for examining the process of the solvent loss or the samples sublimation and decomposition. It can be presumed that the crystal contains crystal water or crystallization solvent. The change in mass by the TGA curve shown depends on a number of factors, containing the sample preparation and the instrument. The change in mass by the TGA test may be slightly different between the different instruments and between the different samples. According to the condition of the instrument used in this test, there is an error tolerance of ±0.1% for the change in mass.

In the context of the present invention, the 2θ values in the X-ray powder diffraction pattern are in degrees (°).

The term "substantially as shown in the figure" refers to at least 50%, or at least 60%, or at least 70%, or at least 80%, or at least 90%, or at least 95%, or at least 99% of the peaks are shown in the X-ray powder diffraction pattern or DSC diagram or Raman spectra pattern or infrared spectra pattern.

The "peak" refers to a feature that a person skilled in the art can recognize without belonging to background noise when referring to a spectrum or/and data that appears in the figure.

The present invention relates to salts and/or crystal forms thereof of (2S,4S)-4-fluoro-1-(4-(3-fluorobenzyloxy)benzyl)pyrrolidine-2-carboxamide, which exist in substantially pure crystalline form.

"Substantially pure" means that a crystalline form is substantially free of another or more crystalline forms, that means the purity of the crystalline form is at least 80%, or at least 85%, or at least 90%, or at least 93%, or at least 95%, or at least 98%, or at least 99%, or at least 99.5%, or at least 99.6%, or at least 99.7%, or at least 99.8%, or at least 99.9%, or crystal form containing other crystal form. The percentage of the other crystals in the total volume or total weight of the crystal form is less than 20%, or less than 10%, or less than 5%, or less than 3%, or less than 1%, or less than 0.5%, or less than 0.1%, or less than 0.01%.

"Substantially free" means that the percentage of one or more other crystalline forms in the total volume or total weight of the crystalline form is less than 20%, or less than 10%, or less than 5%, or less than 4%, or less than 3%, or less than 2%, or less than 1%, or less than 0.5%, or less than 0.1%, or less than 0.01%.

The "relative intensity" (or "relative peak height") in the XRPD pattern means the ratio of the intensity of the other peaks to the intensity of the first strong peak when the intensity of the first strong peak in all the diffraction peaks of the X-ray powder diffraction pattern is 100%.

In the context of the present invention, when used or whether or not used the word, such as "about", it means that within a given value or range of 10% or less, appropriately within 5%, especially within 1%. Or, for those of ordinary skill in the art, the term "about" means within an acceptable standard error range of the mean value. When a number with an N value is made public, any number within N+/−1%, N+/−2%, N+/−3%, N+/−5%, N+/−7%, N+/−8%, or N+/−10% will be opened clearly, wherein "+/−" means plus or minus.

In the present invention, "room temperature" refers to a temperature from about 10° C. to about 40° C. In some embodiments, "room temperature" refers to a temperature from about 20° C. to about 30° C.; in other embodiments, "room temperature" refers to 20° C., 22.5° C., 25° C., 27.5° C. etc.

Pharmaceutical Compositions, Formulations, Administration and Uses of the Salts or their Crystal Forms of the Present Invention The characteristics of the pharmaceutical composition of the present invention include the salt of the compound having formula (I) and/or its crystal form and a pharmaceutically acceptable carrier, adjuvant or excipient. The amount of the salt of the compound or its crystal form in the pharmaceutical composition of the present invention is effective to detectably treat or alleviate central nervous system dysfunction in a patient. The pharmaceutical compositions of the present invention may also optionally contain other therapeutic and/or prophylactic ingredients.

Suitable carriers, adjuvants and vehicles are well known to those skilled in the art and are described in detail in, for example, Ansel H. C. et al., Ansel's Pharmaceutical Dosage Forms and Drug Delivery Systems (2004) Lippincott. Williams & Wilkins, Philadelphia; Gennaro A. R. et al., Remington: The Science and Practice of Pharmacy (2000) Lippincott. Williams & Wilkins, Philadelphia; and Rowe R. C., Handbook of Pharmaceutical Excipients (2005) Pharmaceutical Press, Chicago.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

Various carriers for formulating pharmaceutically acceptable compositions, and well-known techniques for their preparation, are disclosed in Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which are incorporated herein by reference. Except insofar as any conventional carrier medium is incompatible with the compounds of the invention, such as by producing any undesirable biological effect or otherwise interacting in a deleterious manner with any other component(s) of the pharmaceutically acceptable composition, carriers in the known technology and their use are contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Another aspect of the present invention is related to a method for preparing a pharmaceutical composition, the pharmaceutical composition comprises a salt of the compound of the present invention or its crystal form and a pharmaceutically acceptable excipient, carrier, adjuvant, vehicle or a combination thereof, and the method comprises mixing various ingredients. The pharmaceutical composition containing the salt of the compound of the present invention or its crystal form can be prepared at for example environment temperature and under barometric pressure.

The salt of the compound of the invention or the crystal form thereof will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4.410.545. The capsules may also be coated as known by those of skill in the art in order to modify or sustain dissolution of the active ingredient.

In one embodiment, the therapeutic methods disclosed herein comprise administrating to a patient in need of the treatment a safe and effective amount of the salt of the compound of the invention or the crystal form thereof or the pharmaceutical composition comprising the salt of the compound of the invention or the crystal form thereof. Various embodiments of the present invention comprise treating the diseases mentioned in the present invention by administrating to a patient in need of the treatment a safe and effective amount of the salt of the compound of the invention or the crystal form thereof or the pharmaceutical composition comprising the salt of the compound of the invention or the crystal form thereof.

In one embodiment, the salt of the compound of the invention or the crystal form thereof or the pharmaceutical composition comprising the salt of the compound of the invention or the crystal form thereof may be administered by any suitable route of administration, including both systemic administration and topical administration. Systemic administration includes oral administration, parenteral administration, transdermal administration and rectal administration. Typical parenteral administration refers to administration by injection or infusion, including intravenous, intramuscular, and subcutaneous injection or infusion. Topical administration includes application to the skin as well as intraocular, otic, intravaginal, inhaled and intranasal administration. In one embodiment, the salt of the compound of the invention or the crystal form thereof or the pharmaceutical composition comprising the salt of the compound of the invention or the crystal form thereof may be administered orally. In another embodiment, the salt of the compound of the invention or the crystal form thereof or the pharmaceutical composition comprising the salt of the compound of the invention or the crystal form thereof may be administered by inhalation. In another embodiment, the salt of the compound of the invention or the crystal form thereof or the pharmaceutical composition comprising the salt of the compound of the invention or the crystal form thereof may be administered intranasally.

In one embodiment, the salt of the compound of the invention or the crystal form thereof or the pharmaceutical composition comprising the salt of the compound of the invention or the crystal form thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the salt of the compound of the invention or the crystal form thereof or the pharmaceutical composition comprising the salt of the compound of the invention or the crystal form thereof depend on the pharmacokinetic properties of the salt of the compound, such as absorption, distribution, and half-life, which can be determined by the skilled artisan. In addition, suitable dosing regimens, including the duration such regimens are administered, for the salt of the compound of the invention or the crystal form thereof or the pharmaceutical composition comprising the salt of the compound of the invention or the crystal form thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The salt of the compound of the invention or the crystal form thereof may be administered either simultaneously with, or before or after, one or more other therapeutic agents. The salt of the compound of the invention or the crystal form thereof may be administered separately, by the same or different route of administration, or together in the same pharmaceutical composition as the other agents.

The term "therapeutically effective amount," as used herein, refers to the total amount of each active ingredient sufficient to exhibit a beneficial therapeutic effect. For example, administering or bringing into equilibrium an amount sufficient to treat, cure or alleviate the symptoms of a disease. The effective amount required for a particular treatment regimen will depend on a variety of factors, including the disease being treated, the severity of the disease, the activity of the specific drug being used, the mode of administration, the clearance of the specific drug, duration of treatment, concomitant drugs, age, weight, sex, diet and patient's health, etc. A description in the art of other factors to be considered for a "therapeutically effective amount" can be found in Gilman et al., eds., Goodman and Gilman's: The Pharmacological Bases of Therapeutics, 8th ed., Pergamon Press, 1990; Remington's Pharmaceutical Sciences, 17th ed., Mack Publishing Company, Easton, Pa., 1990. When a therapeutically effective amount of the compound of the present invention is 0.1-200 mg/kg administered orally, intraperitoneally or intravenously, the compound of the present invention is active in vivo.

The optimal therapeutically effective amount to be administered can be readily determined by one skilled in the art and will vary substantially with the strength of the formulation, the mode of administration and the progression of the disease or condition being treated. In addition, factors associated with the particular subject being treated, including subject age, body weight, meals and time of administration, will result in the need to adjust dosage to appropriate therapeutically effective levels.

The term "administration" refers to providing a therapeutically effective amount of a drug to an individual, including oral, sublingual, intravenous, subcutaneous, transdermal, intramuscular, intradermal, intrathecal, epidural, intraocular, intracranial, inhalation, rectal, vaginal, etc. Dosage forms include ointments, lotions, tablets, capsules, pills, dispersible powders, granules, suppositories, pellets, lozenges, injections, sterile solutions or non-aqueous solutions, suspensions, emulsions, patches etc. The active ingredient is compounded with a non-toxic pharmaceutically acceptable carrier (such as dextrose, lactose, gum arabic, gelatin, mannitol, starch paste, magnesium trisilicate, talc, corn starch, keratin, silica gel, potato starch, urea, dextran, etc.).

The preferred route of administration will vary with the clinical features, and the dosage must be varied depending on the condition of the patient being treated, and the physician will determine the appropriate dosage according to the individual patient. The therapeutically effective amount per unit dose will depend on body weight, physiology and the chosen vaccination regimen. The amount of the compound per unit dose refers to the weight of the compound per administration, excluding the weight of the carrier (the drug contains the carrier). The pharmaceutical composition comprising the compound represented by the formula (I) as defined above comprises about 0.1 mg to about 500 mg of one or more active ingredients per unit dose such as capsules, tablets, powder injections, teaspoonfuls, suppositories, etc., most preferably 1-10 mg.

The salts of the compounds provided by the present invention or their crystal forms and pharmaceutical compositions can be used in the manufacture of a medicament for the prevention, treatment or alleviation of diseases regulated by MAO-B in patients, can also be used in the manufacture of a medicament for the prevention, treatment or alleviation of neurodegenerative diseases, psychosis or cancer, and can also be used in the manufacture of a medicament for inhibiting the activity of MAO-B.

Specifically, the amount of the compound in the pharmaceutical composition of the present invention can effectively, detectably and selectively inhibit the activity of MAO-B, and the salt of the compound of the present invention or its crystal form can be used as a drug for treating diseases regulated by MAO-B, such as Parkinson's disease.

The salt of the compound of the present invention or its crystal form would be useful for, but is not limited to, preventing, treating or alleviating neurodegenerative diseases by administering to the patient the salt of the compound of the present invention or its crystal form or the pharmaceutical composition disclosed herein in an effective amount. The neurodegenerative disease further includes, but is not limited to, Parkinson's disease, cerebral ischemia, Alzheimer's disease, amyotrophic lateral sclerosis, hearing loss caused by aging, dementia, retinal degeneration, macular degeneration, glaucoma, bovine spongiform encephalopathy, Huntington's disease, Creutzfeldt-Jakob disease, ataxia-telangiectasia, cerebellar atrophy, spinal muscular atrophy, primary lateral sclerosis, or multiple sclerosis.

The salt of the compound of the present invention or its crystal form would be useful for, but is not limited to, preventing, treating or alleviating psychosis by administering to the patient the salt of the compound of the present invention or its crystal form or a pharmaceutical composition disclosed herein in an effective amount. The psychosis is schizophrenia and/or anxiety disorder, wherein schizophrenia further includes, but is not limited to, short-term psychosis, paranoia, schizophrenia and schizophrenia-like mental disorder; wherein anxiety disorder further includes, but is not limited to, panic disorder, obsessive-compulsive disorder, post-traumatic stress disorder, social phobia or social anxiety disorder, specific phobia, and general anxiety disorder.

The salt of the compound of the present invention or its crystal form would be useful for, but is not limited to, preventing, treating or alleviating cancer by administering to the patient the salt of the compound of the present invention or its crystal form or the pharmaceutical composition disclosed herein in an effective amount. The cancer further includes, but is not limited to, prostate cancer, breast cancer, testicular cancer, colorectal cancer, lung cancer, brain tumor, kidney tumor or blood cancer.

An "effective amount" or "effective dose" of the salt of the compound of the present invention or its crystal form or the pharmaceutically acceptable composition is an amount that is effective in treating or lessening the severity of one or more of the aforementioned disorders. The salt of the compound of the present invention or its crystal form or the pharmaceutically acceptable composition, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. The salt of the compound of the present invention or its crystal form or the pharmaceutically acceptable composition can also be administered with one or more other therapeutic agents as discussed above.

Besides being useful for human treatment, the salt of the compound of the present invention or its crystal form or the pharmaceutically acceptable composition is also useful for veterinary treatment of mammals such as companion animals, exotic animals and farm animals. In other embodiments, the animals disclosed herein include horses, dogs, and cats.

DESCRIPTION OF THE PREFERRED EMBODIMENTS

Figure 1:
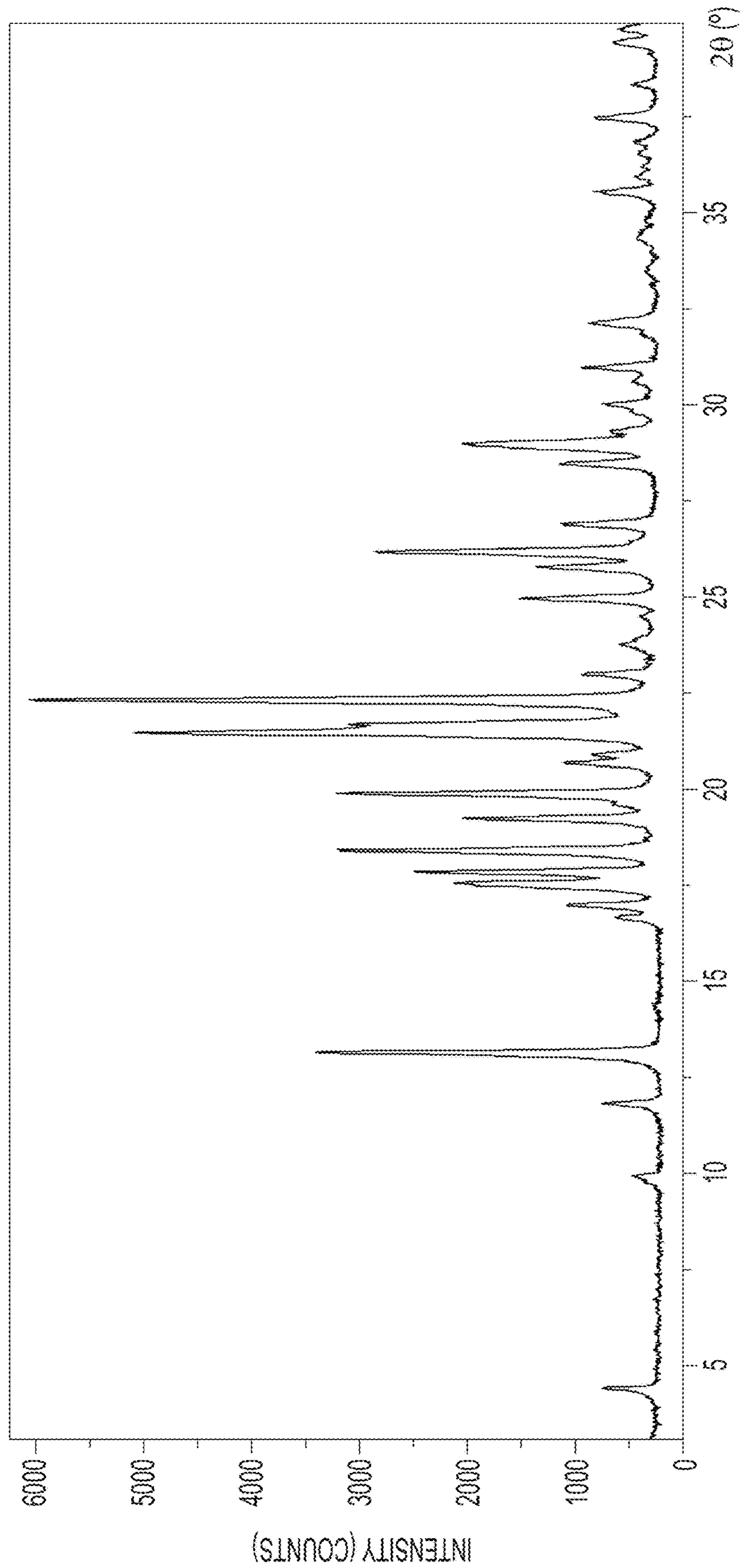
FIG. 1 is an X-ray powder diffraction (XRPD) pattern of the mesylate crystal form A of the compound represented by formula (I).

The invention will now be further described by way of example without limiting the invention to the scope of the invention.

The X-ray powder diffraction analysis method used in the present invention was an Empyrean diffractometer, and an X-ray powder diffraction pattern was obtained using Cu-Kα radiation (45 KV, 40 mA). The powdery sample was prepared as a thin layer on a monocrystalline silicon sample rack and placed on a rotating sample stage, analyzed at a rate of 0.0167 steps in the range of 3°-40°. Data Collector software was used to collect data, HighScore Plus software was used to process data, and Data Viewer software was used to read data.

The differential scanning calorimetry (DSC) analysis method used in the present invention is a differential scanning calorimeter using a TA Q2000 module with a thermal analysis controller. Data were collected and analyzed using TA Instruments Thermal Solutions software. Approximately 1-5 mg of the sample was accurately weighed into a specially crafted aluminum crucible with a lid and analyzed from room temperature to about 300° C. using a linear heating device at 10° C./min. During use, the DSC chamber was purged with dry nitrogen.

The solubility of the present invention was determined using an Agilent 1200 High Performance Liquid Chromatograph DAD/VWD detector with an Agilent XDB-C18 model (4.6×50 mm, 5 μm). Detection wavelength was 266 nm, flow rate was 1.0 mL/min, the column temperature was 35° C., mobile phase A: acetonitrile/0.01 M ammonium acetate=10190 (V/V), analysis methods: acetonitrile/mobile phase A=70/30 (V/V), running time was 10 minutes.

EXAMPLES

For the specific synthesis method of the compound represented by formula (I): (2S,4S)-4-fluoro-1-(4-(3-fluorobenzyloxy)benzyl)pyrrolidine-2-carboxamide, refer to Example 1 in the international application WO 2019170115 A1.

Examples

Example 1: Mesylate Crystal Form A of the Present Invention

1. Preparation of Mesylate Crystal Form A

The compound having formula (I) (11.87 g) and ethyl acetate (180 mL) were mixed at room temperature, and then heated to 50° C. to dissolve; methanesulfonic acid (3.95 g) was added to ethyl acetate (20 mL), after stirring evenly, it was slowly added dropwise to the aforementioned ethyl acetate solution, and crystals were precipitated, filtered, and dried in vacuo at 60° C. to obtain off-white solid powder, which is mesylate crystal form A.

2. Identification of Mesylate Crystal Form A (1) Analysis and identification by Empyrean X-ray powder diffraction (XRPD): Cu-Kα radiation was used and the pattern comprises the following characteristic peaks expressed as 2θ at: 4.38°, 11.79°, 13.11°, 16.63°, 16.95°, 17.46°, 17.55°, 17.81°, 18.37°, 19.21°, 19.85°, 20.65°, 20.87°, 21.43°, 21.65°, 22.28°, 22.95°, 24.92°, 25.74°, 26.14°, 26.86°, 28.42°, 28.92°, 29.28°, 29.95°, 30.94°, 32.09° and 35.49°. There is an error tolerance of 0.2°.

(2) Analysis and identification by TA Q2000 Differential Scanning Calorimetry: the scanning speed was 10° C./min and the diagram comprises an endothermic peak of 238.12° C. There is an error tolerance of ±3° C.

Example 2: Mesylate Crystal Form B of the Present Invention

1. Preparation of Mesylate Crystal Form B

The compound represented by formula (I) (100 mg) was added to ethyl acetate (2 mL), and then methanesulfonic acid (42 mg) was added. The mixture was reacted overnight at room temperature. The reaction was stopped, and the mixture was filtered with suction, and dried to obtain off-white solid powder, which is mesylate crystal form B.

2. Identification of Mesylate Crystal Form B (1) Analysis and identification by Empyrean X-ray powder diffraction (XRPD): Cu-Kα radiation was used and the pattern comprises the following characteristic peaks expressed as 2θ at: 4.19°, 8.33°, 12.52°, 16.72°, 17.60°, 20.19°, 21.08°, 22.35°, 25.22°, 29.50° and 33.85°. There is an error tolerance of 0.2°.

(2) Analysis and identification by TA Q2000 Differential Scanning Calorimetry: the scanning speed was 10° C./min and the diagram comprises an endothermic peak of 230.55° C. There is an error tolerance of ±3° C.

Example 3: Mesylate Crystal Form C of the Present Invention

1. Preparation of Mesylate Crystal Form C

The mesylate crystal form A (50 mg) of the compound represented by formula (I) was added into a mixed solvent of 1,4-dioxane (0.5 mL) and isopropanol (0.5 mL), and the mixture was suspended and stirred at room temperature for 24 h. The mixture was filtered with suction to obtain off-white solid powder, which is mesylate crystal form C.

2. Identification of Mesylate Crystal Form C

Analysis and identification by Empyrean X-ray powder diffraction (XRPD): Cu-Ku radiation was used and the pattern comprises the following characteristic peaks expressed as 2θ at: 4.22°, 12.56°, 16.77°. 17.66°, 17.84°, 18.27°, 18.82°, 19.44°, 20.25°, 21.18°, 22.88°, 23.11°, 26.13° and 33.88°. There is an error tolerance of ±0.20.

Example 4: Mesylate Crystal Form D of the Present Invention

1. Preparation of Mesylate Crystal Form D

The mesylate crystal form A (30 mg) of the compound represented by formula (I) was dissolved in methanol (0.9 mL), and then the solution was dropwise added into 1,4-dioxane (1.5 mL). The mixture was reacted at 0° C. overnight. The reaction was stopped, and the mixture was filtered with suction to obtain off-white solid powder, which is mesylate crystal form D.

2. Identification of Mesylate Crystal Form D

Analysis and identification by Empyrean X-ray powder diffraction (XRPD): Cu-Kα radiation was used and the pattern comprises the following characteristic peaks expressed as 2θ at: 4.32°, 8.58°, 9.59°, 12.12°. 13.54°, 15.41°, 16.33°, 17.70°, 18.47°, 19.21°, 20.37°, 21.48°, 21.99°, 23.19°, 23.76°, 24.57°, 25.11°, 25.94°, 27.29° and 28.89°. There is an error tolerance of 0.2°.

Example 5: Mesylate Crystal Form E of the Present Invention

1. Preparation of Mesylate Crystal Form E

The mesylate crystal form B (300 mg) of the compound represented by formula (I) was added into 1,4-dioxane (10 mL), and the mixture was suspended and stirred at 70° C. for 48 h. The mixture was filtered with suction, and dried to obtain off-white solid powder, which is mesylate crystal form E.

2. Identification of Mesylate Crystal Form E (1) Analysis and identification by Empyrean X-ray powder diffraction (XRPD): Cu-Kα radiation was used and the pattern comprises the following characteristic peaks expressed as 2θ at: 4.29°, 8.52°, 9.53°, 12.07°, 12.80°, 13.50°, 15.13°, 15.41°, 16.27°, 17.63°, 18.40°, 19.14°, 20.31°, 21.42°, 21.860, 24.480, 26.14°, 27.54°, 28.06°, 28.79° and 34.89°. There is an error tolerance of 0.2°.

(2) Analysis and identification by TA Q2000 Differential Scanning Calorimetry: the scanning speed was 10° C. min and the diagram comprises an endothermic peak of 238.07° C. There is an error tolerance of t 3° C.

Example 6: Mesylate Crystal Form F of the Present Invention

1. Preparation of Mesylate Crystal Form F

The mesylate crystal form B (50 mg) of the compound represented by formula (I) was added into 1,4-dioxane (1 mL), and the mixture was suspended and stirred at room temperature for 24 h. The mixture was filtered with suction to obtain off-white solid powder, which is mesylate crystal form F.

2. Identification of Mesylate Crystal Form F

Analysis and identification by Empyrean X-ray powder diffraction (XRPD): Cu-Ku radiation was used and the pattern comprises the following characteristic peaks expressed as 2θ at: 4.40°, 10.920, 11.77°, 13.13°, 16.74°, 17.53°, 17.82°, 18.38°, 19.19°, 19.860, 20.86°, 21.41°, 22.27°, 23.00°, 25.75°, 28.94°, 29.96° and 30.93°. There is an error tolerance of ±0.20.

Example 7: Mesylate Crystal Form G of the Present Invention

1. Preparation of Mesylate Crystal Form G

The mesylate crystal form A (30 mg) of the compound represented by formula (I) was dissolved in methanol (0.9 mL), and dimethyl carbonate (1.5 mL) was added dropwise. The mixture was reacted at 0° C. overnight. The reaction was stopped, and the mixture was filtered with suction to obtain off-white solid powder, which is mesylate crystal form G 2. Identification of Mesylate Crystal Form G Analysis and identification by Empyrean X-ray powder diffraction (XRPD): Cu-Ku radiation was used and the pattern comprises the following characteristic peaks expressed as 2θ at: 6.65°, 7.160, 8.780, 9.01°, 10.17°, 11.59°, 12.12°, 12.960, 13.130, 14.360, 15.930, 17.37°, 17.64°, 18.36°, 18.68°, 19.19°, 19.74°, 20.54°, 21.410, 22.18°, 23.010 and 26.140. There is an error tolerance off 0.2°.

Example 8: Hydrochloride Crystal Form A of the Present Invention

1. Preparation of Hydrochloride Crystal Form A

The compound represented by formula (I) (100 mg) was added to ethyl acetate (2 mL), and then hydrochloric acid (40 mg, mass fraction 36-38%) was added. The mixture was reacted overnight at room temperature. The reaction was stopped, and the mixture was filtered with suction, and dried to obtain off-white solid powder, which is hydrochloride crystal form A.

2. Identification of Hydrochloride Crystal Form A (1) Analysis and identification by Empyrean X-ray powder diffraction (XRPD): Cu-Kα radiation was used and the pattern comprises the following characteristic peaks expressed as 2θ at: 7.05°. 7.540, 12.49°. 14.13°, 15.16°, 16.49°, 18.32°, 19.34°, 19.92°, 21.28°, 22.50°, 23.63°, 25.40°, 25.86°, 26.93°, 27.42°, 27.92°, 29.21°. 29.38°, and 35.14°. There is an error tolerance off 0.20.

(2) Analysis and identification by TA Q2000 Differential Scanning Calorimetry: the scanning speed was 10° C./min and the diagram comprises an endothermic peak of 264.34° C. There is an error tolerance of ±3° C.

Example 9: Maleate Crystal Form A of the Present Invention

1. Preparation of Maleate Crystal Form A

The compound represented by formula (I) (100 mg) was added to ethyl acetate (2 mL), and then maleic acid (41 mg) was added. The mixture was reacted overnight at room temperature. The reaction was stopped, and the mixture was filtered with suction, and dried to obtain off-white solid powder, which is maleate crystal form A.

2. Identification of Maleate Crystal Form A (1) Analysis and identification by Empyrean X-ray powder diffraction (XRPD): Cu-Kα radiation was used and the pattern comprises the following characteristic peaks expressed as 2θ at: 6.25°, 9.37°, 9.66°, 15.08°, 16.60°, 17.74°, 18.41°, 18.93°, 20.54°, 21.06°, 21.79°, 22.95°, 24.72°, 25.38°, 27.28°, 27.99°, 29.40°, 30.07°, 31.85°, 33.730 and 34.64°. There is an error tolerance of 0.20.

(2) Analysis and identification by TA Q2000 Differential Scanning Calorimetry: the scanning speed was 10° C. imin and the diagram comprises an endothermic peak of 218.14° C. There is an error tolerance of ±3° C.

Example 10: p-Toluenesulfonate Crystal Form A of the Present Invention

1. Preparation of p-Toluenesulfonate Crystal Form A

The compound represented by formula (I) (100 mg) was added to ethyl acetate (3 mL), and then p-toluenesulfonic acid (71 mg) was added. The mixture was reacted overnight at room temperature. The reaction was stopped, and the mixture was filtered with suction, and dried to obtain off-white solid powder, which is p-toluenesulfonate crystal form A.

2. Identification of p-Toluenesulfonate Crystal Form A (1) Analysis and identification by Empyrean X-ray powder diffraction (XRPD): Cu-Ku radiation was used and the pattern comprises the following characteristic peaks expressed as 2θ at: 4.25°, 8.44°, 9.350, 9.59°, 11.84°, 13.26°, 13.55°, 15.10°, 15.49°, 16.63°, 17.75°, 18.24°, 18.85°, 19.17°, 19.59°, 21.00°, 21.15°, 21.43°, 22.83°, 23.20°, 24.63°, 25.46°, 25.75°, 25.96°, 28.31°, 29.06° and 30.34°. There is an error tolerance of ±0.2°.

(2) Analysis and identification by TA Q2000 Differential Scanning Calorimetry: the scanning speed was 10° C. min and the diagram comprises endothermic peaks of 130.74° C. and 242.83° C. There is an error tolerance of ±3° C.

Example 11 the Pharmacokinetics Test of the Salt of the Present Invention or its Crystal Form The test samples (that is, the salt of the present invention or its crystal form, or the compound represented by formula (I) of the present invention) were filled into capsules for oral administration.

Three 0.2-0.3 kg male Beagle dogs were taken orally administered capsules containing the test sample at a dose of 5 mg/kg, and blood was collected at time points of 0.25, 0.5, 1.0, 2.0, 5.0, 7.0 and 24 h. Standard curve was plotted based on concentrations of the samples in a suitable range, the concentration of the test sample in the plasma sample was measured and quantified by AB SCIEX API5500 LC-MS/MS at MRM mode. Pharmacokinetic parameters were calculated according to drug concentration-time curve using a noncompartmental method by WinNonLin 6.3 software. Results are as shown in Table 1.

TABLE 1

Pharmacokinetic experimental data of the salt of the present invention or its crystal form

| Test sample | $T_{max}$ (h) | $C_{max}$ (ng/ml) | $AUC_{last}$ (h*ng/ml) |
|---|---|---|---|
| Example 2 (mesylate crystal form B) | 1 | 415 | 939 |
| Example 8 (hydrochloride crystal form A) | 0.7 | 143 | 378 |

TABLE 1-continued

| Pharmacokinetic experimental data of the salt of the present invention or its crystal form | | | |
|---|---|---|---|
| Test sample | $T_{max}$ (h) | $C_{max}$ (ng/ml) | $AUC_{last}$ (h*ng/ml) |
| Example 9 (maleate crystal form A) | 3.4 | 151 | 450 |
| Example 10 (p-toluenesulfonate crystal form A) | 2.2 | 162 | 470 |
| Compound represented by formula (I) | 0.8 | 256 | 548 |

Conclusion:

As can be seen from Table 1, compared with the compound represented by formula (I), hydrochloride crystal form A, maleate crystal form A, and p-toluenesulfonate crystal form A of the compound represented by formula (I), the mesylate crystal form B of the present invention has higher blood drug concentration and greater exposure in rats, and has better pharmacokinetic properties.

Example 12 the Stability Test of the Salt of the Present Invention or its Crystal Form (1) High temperature test: a batch of the test samples were taken into the flat weighing bottles, spread into a thin layer with a thickness of ≤5 mm. The above weighing bottles were stored at 40° C.±2° C./75%±5% RH and 60° C.±2° C./75% f 5% RH for 30 days in an incubator. On the 5th, 10th, and 30th days, samples were taken for detection according to the key stability inspection items: the color change of the sample was observed, the purity of the sample was determined by HPLC.

(2) High humidity test: a batch of the test samples were taken into the flat weighing bottles, spread into a thin layer with a thickness of ≤5 mm, and stored for 30 days at 25° C., RH 75%±5% or RH 90%±5%. On the 5th, 10th, and 30th days, samples were taken for detection according to the key stability inspection items: the color change of the sample was observed, the purity of the sample was determined by HPLC.

(3) Light test: a batch of the test samples were taken into the flat weighing bottles, spread into a thin layer of ≤5 mm thick, and placed in a light box (with an ultraviolet lamp) with an open mouth. The test samples were stored under the condition of illuminance of 4500±500 lx and ultraviolet light ≥0.7 w·h/$m^2$ for 30 days. On the 5th, 10th, and 30th days, samples were taken for detection according to the key stability inspection items: the color change of the sample was observed, the purity of the sample was determined by HPLC.

The stability test results areas shown in Table 2:

It can be seen from the experimental results that under the conditions of high temperature, high humidity and light, the appearance and purity of the mesylate crystal form B of the present invention have no obvious change. That is, the mesylate crystal form B of the present invention has good stability under various setting conditions and is suitable for pharmaceutical use.

Example 13 the Hygroscopicity Test of the Salt of the Present Invention or its Crystal Form 1. Test Method 1) A dry stoppered glass weighing bottle (50 mm in outer diameter, 15 mm in height) was placed in a constant temperature desiccator (the lower part was placed in a saturated ammonium chloride solution) at 25° C.±1° C. the day before, and accurately weighed ($m_1$).

2) An appropriate amount of the test sample was taken and spread in the above weighing bottle. The thickness of the test sample was generally about 1 mm, and it was precisely weighed ($m_2$).

3) The weighing bottle was opened and placed together with the bottle cap under the above constant temperature and humidity conditions for 24 hours.

4) The weighing bottle was closed with the bottle cap, and accurately weighed ($m_3$). Calculate: weight gain $\%=(m_3-m_2)/(m_2-m_1)\times 100\%$.

5) Judgment of hygroscopicity results is as shown in Table 3.

TABLE 3

| Judgment of hygroscopicity results | | |
|---|---|---|
| | The hygroscopicity feature | The hygroscopicity gain |
| 1 | Deliquescence | Absorb enough water to form a liquid |
| 2 | Highly hygroscopicity | Not less than 15% |
| 3 | Hygroscopicity | Less than 15% but not less than 2% |
| 4 | Slightly hygroscopicity | Less than 2% but not less than 0.2% |
| 5 | No or almost none hygroscopicity | Less than 0.2% |

TABLE 2

Stability test results of the mesylate crystal form B of the present invention

| | | Condition | | | | | | | | | | | | | | |
|---|---|---|---|---|---|---|---|---|---|---|---|---|---|---|---|---|
| | | High temperature (40° C., RH 75% ± 5%) | | | High temperature (60° C., RH 75% ± 5%) | | | High humidity (25° C., RH 75% ± 5%) | | | High humidity (25° C., RH 90% ± 5%) | | | Light | | |
| Project | 0 day | 5 days | 10 days | 30 days | 5 days | 10 days | 30 days | 5 days | 10 days | 30 days | 5 days | 10 days | 30 days | 5 days | 10 days | 30 days |
| Outward | Off-white solid | Off-white solid | Off-white solid | Off-white solid | Off-white solid | Off-white solid | Off-white solid | Off-white solid | Off-white solid | Off-white solid | Off-white solid | Off-white solid | Off-white solid | Off-white solid | Off-white solid | Off-white solid |
| Purity/% | 99.74 | 99.74 | 99.70 | 99.68 | 99.72 | 99.64 | 99.68 | 99.80 | 99.69 | 99.72 | 99.80 | 99.69 | 99.73 | 99.70 | 99.64 | 99.64 |

2. The Hygroscopicity Test Results are as Shown in Table 4:

TABLE 4

The hygroscopicity test results of the mesylate crystal form B of the present invention

| Experiment No. | $m_1$ (mg) | $m_2$ (mg) | $m_3$ (mg) | Hygroscopicity gain (%) | Conclusion |
|---|---|---|---|---|---|
| 1 | 29709.14 | 30713.57 | 30714.77 | 0.12 | No or almost none hygroscopicity |

Conclusion:

It can be seen from the experimental results that the mesylate crystal form B of the present invention has no or almost no hygroscopicity, and is not easily affected by high humidity to deliquescence.

Example 14 the Solubility Test of the Salt of the Present Invention or its Crystal Form The test samples were placed in organic ultrapure water at 37 O(C to prepare a supersaturated solution. After shaking for 24 h, the mixture was filtered with an aqueous filter membrane to obtain the filtrate, and the solubility of the target sample in water was detected by HPLC. Results are as shown in Table 5.

TABLE 5

Solubility experimental data of the salt of the present invention or its crystal form

| Test sample | Concentration of compound represented by formula (I) in saturated aqueous solution (μg/mL) |
|---|---|
| Example 2 (mesylate crystal form B) | 21161.79 |
| Example 8 (hydrochloride crystal form A) | 4719.01 |
| Example 9 (maleate crystal form A) | 575.35 |
| Example 10 (p-toluenesulfonate crystal form A) | 1571.18 |
| Compound represented by formula (I) | 11.40 |

Conclusion:

The experimental results show that, compared with the compound represented by formula (I), hydrochloride crystal form A, maleate crystal form A. and p-toluenesulfonate crystal form A of the compound represented by formula (I), the mesylate crystal form B of the present invention has higher solubility in water, so it has good druggability and is suitable for formulation development.

The foregoing description is merely a basic illustration of the present invention and any equivalent transformation made in accordance with the technical solution of the present invention is intended to be within the scope of the present invention.

Reference throughout this specification to "an embodiment", "some embodiments", "one embodiment", "another example", "an example", "a specific example", or "some examples" means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A salt of the compound having formula (I), (I)

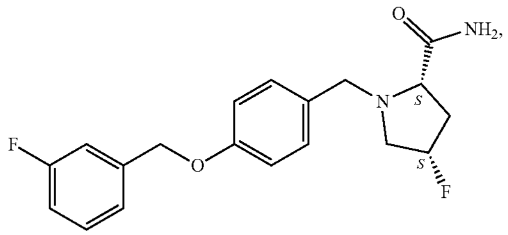

wherein, the salt is an organic acid salt or an inorganic acid salt, wherein the salt is mesylate, wherein the mesylate is mesylate crystal form B, and the X-ray powder diffraction pattern of the mesylate crystal form B comprises peaks expressed as 2θ at: 4.19°±0.2°, 12.52°±0.2°, 16.72°±0.2°, 17.60°±0.2°, 20.19°±0.2°, 21.08°±0.2°.

2. The salt of claim 1, wherein the mesylate is mesylate crystal form B, and the X-ray powder diffraction pattern of the mesylate crystal form B comprises peaks expressed as 2θ at: 4.19°±0.2°, 8.33°±0.2°, 12.52°±0.2°, 16.72°±0.2°, 17.60°±0.2°, 20.19°±0.2°, 21.08°±0.2°, 22.35°±0.2°, 25.22°±0.2°, 29.50°±0.2°, 33.85°±0.2°.

Figure 2:
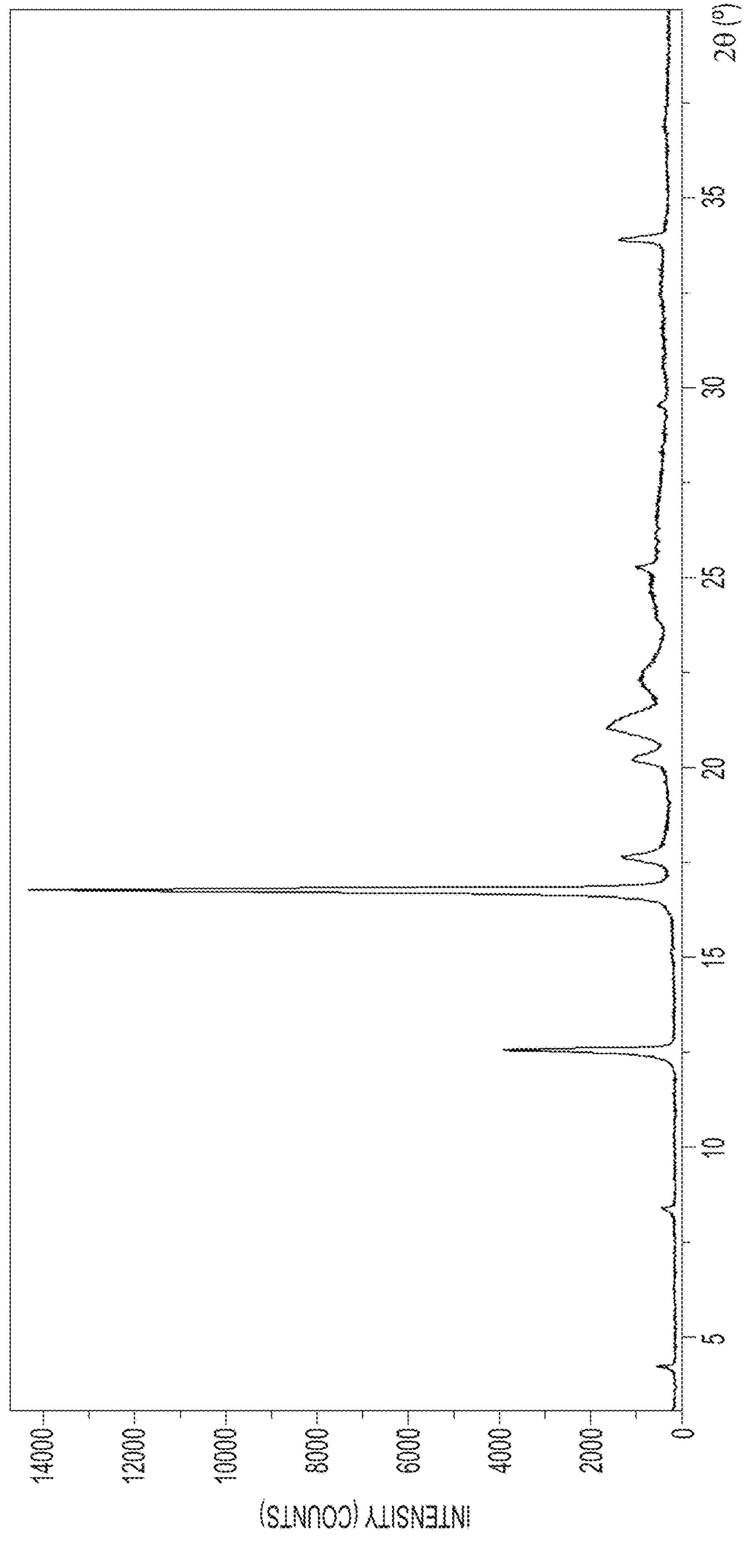
FIG. 2 is an X-ray powder diffraction (XRPD) pattern of the mesylate crystal form B of the compound represented by formula (I).
Figure 3:
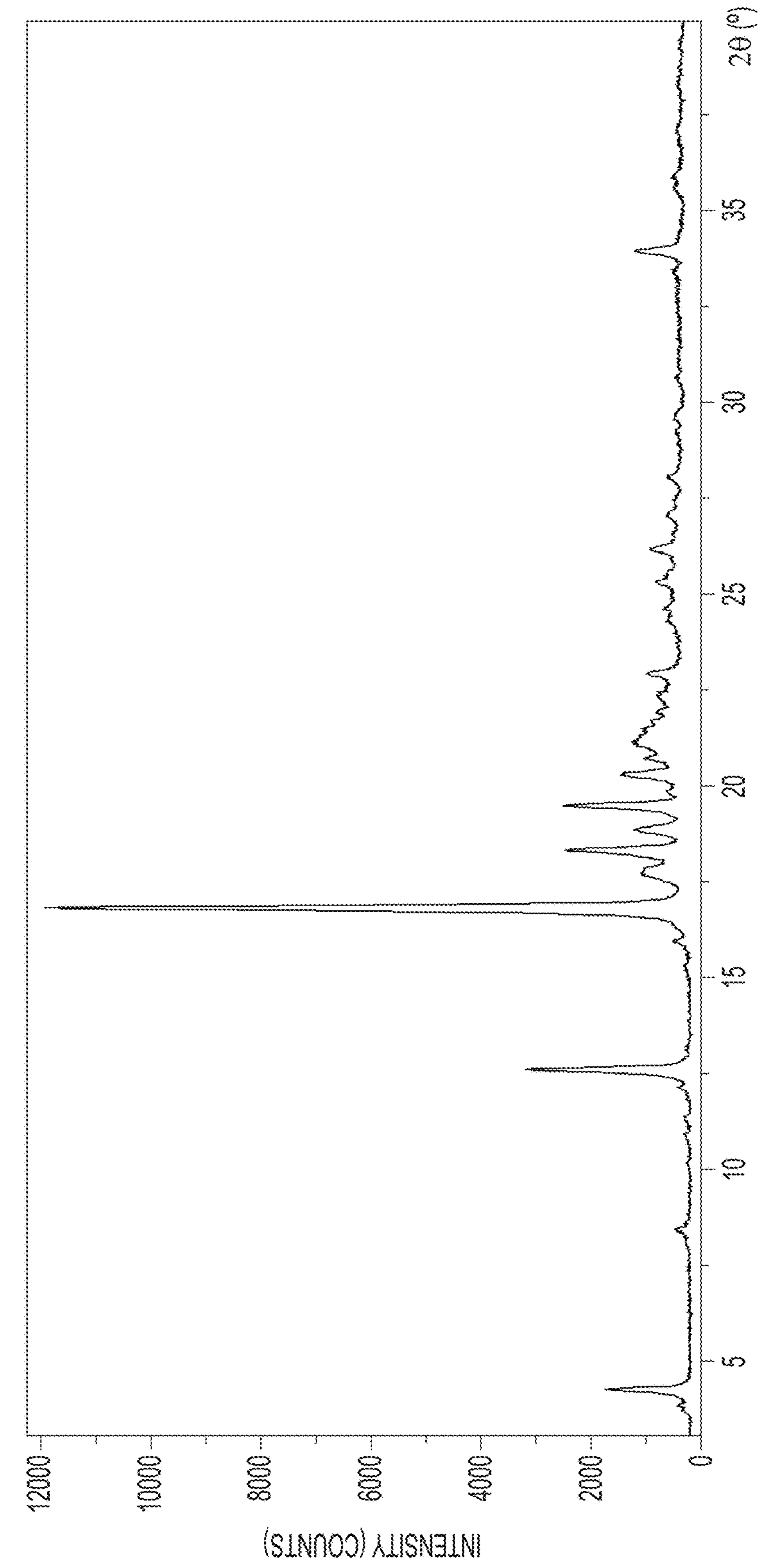
FIG. 3 is an X-ray powder diffraction (XRPD) pattern of the mesylate crystal form C of the compound represented by formula (I).
Figure 4:
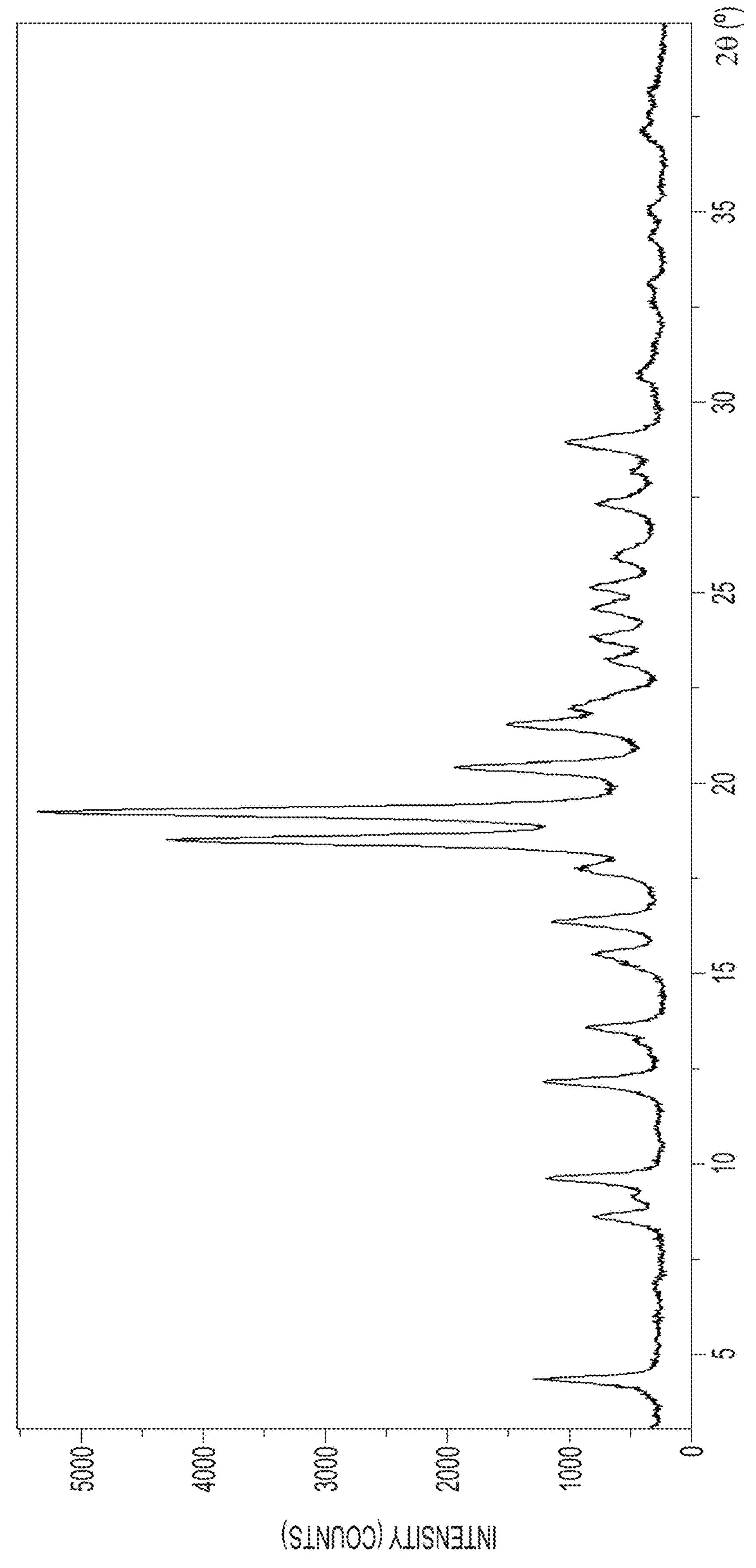
FIG. 4 is an X-ray powder diffraction (XRPD) pattern of the mesylate crystal form D of the compound represented by formula (I).
Figure 5:
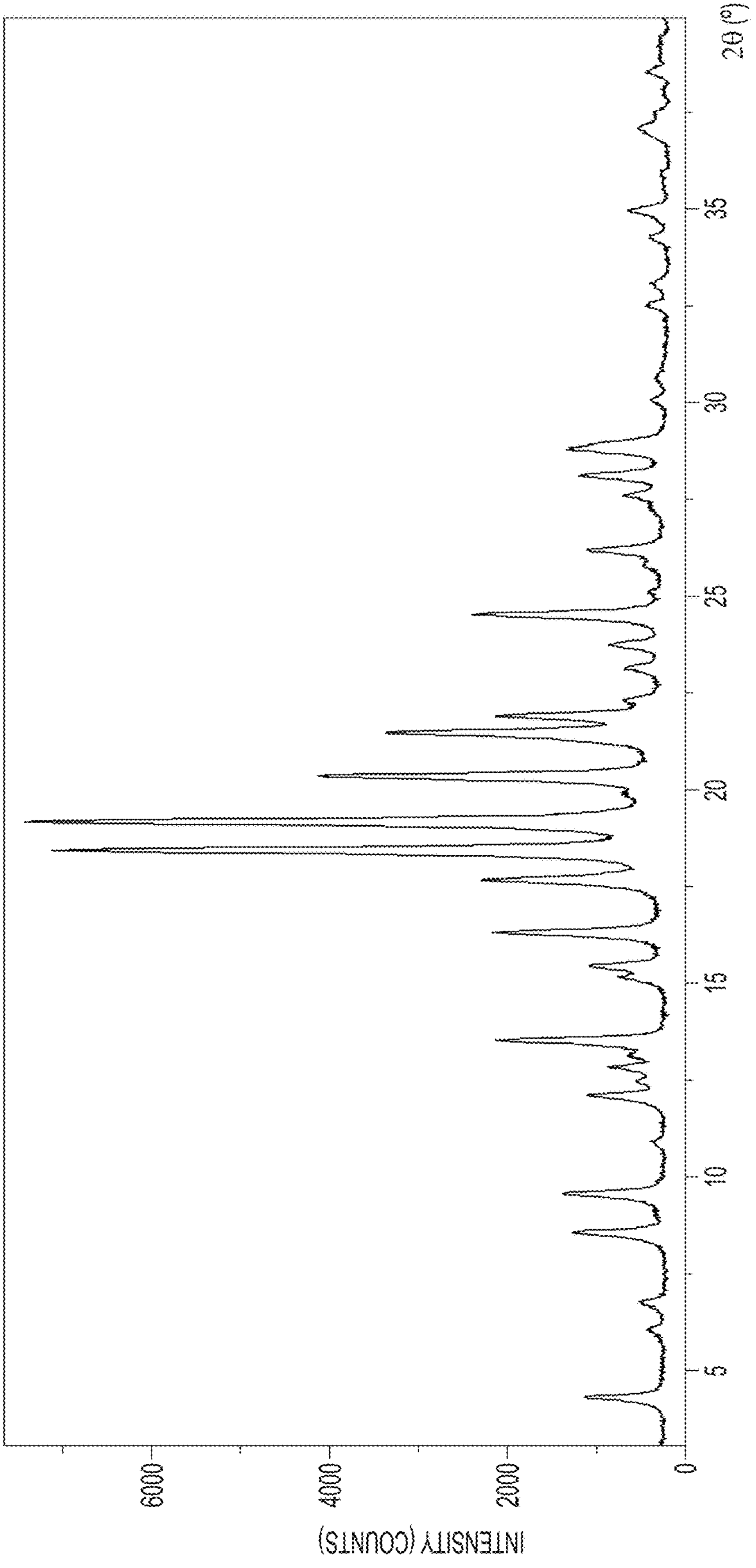
FIG. 5 is an X-ray powder diffraction (XRPD) pattern of the mesylate crystal form E of the compound represented by formula (I).
Figure 6:
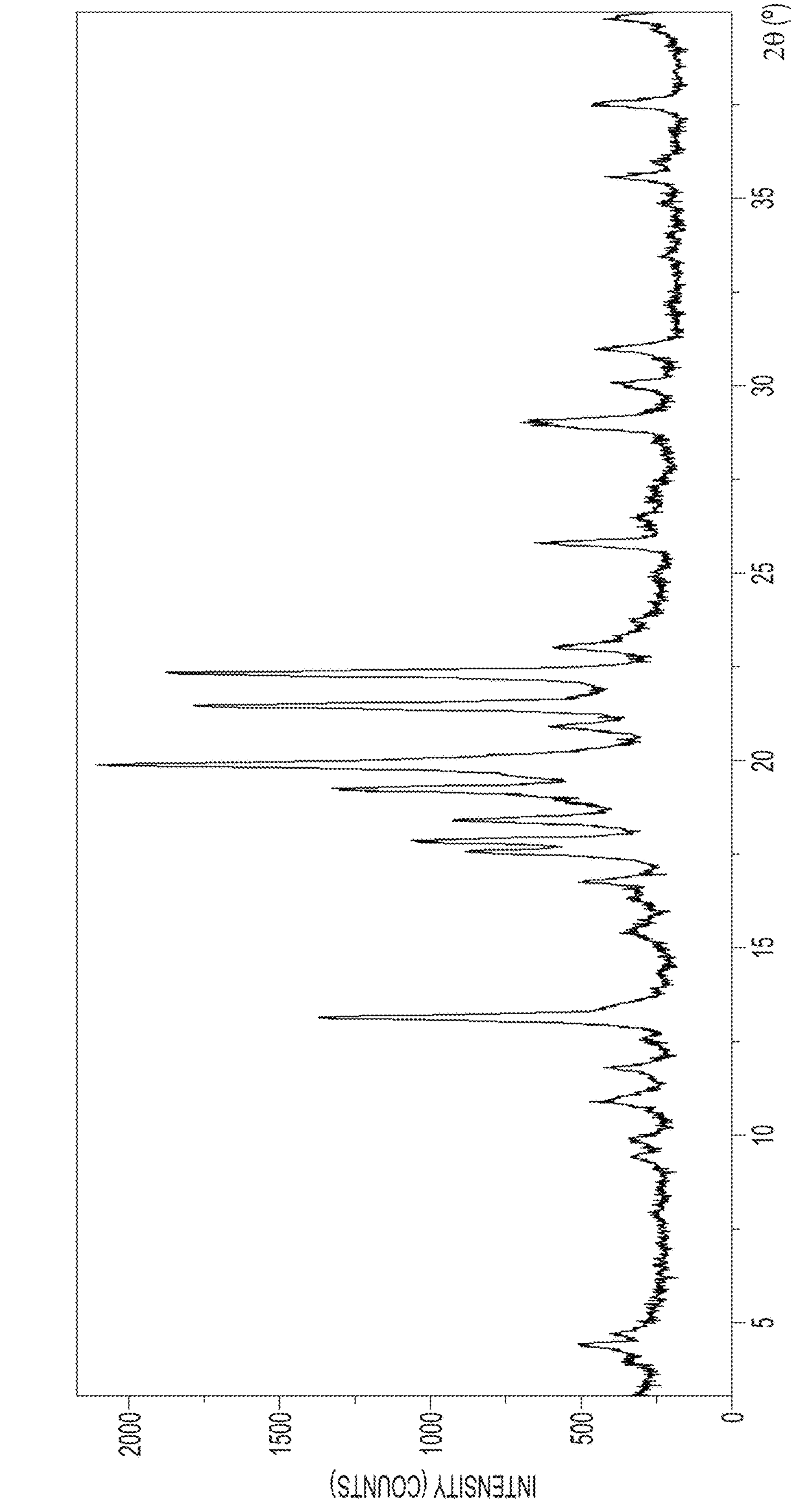
FIG. 6 is an X-ray powder diffraction (XRPD) pattern of the mesylate crystal form F of the compound represented by formula (I).
Figure 7:
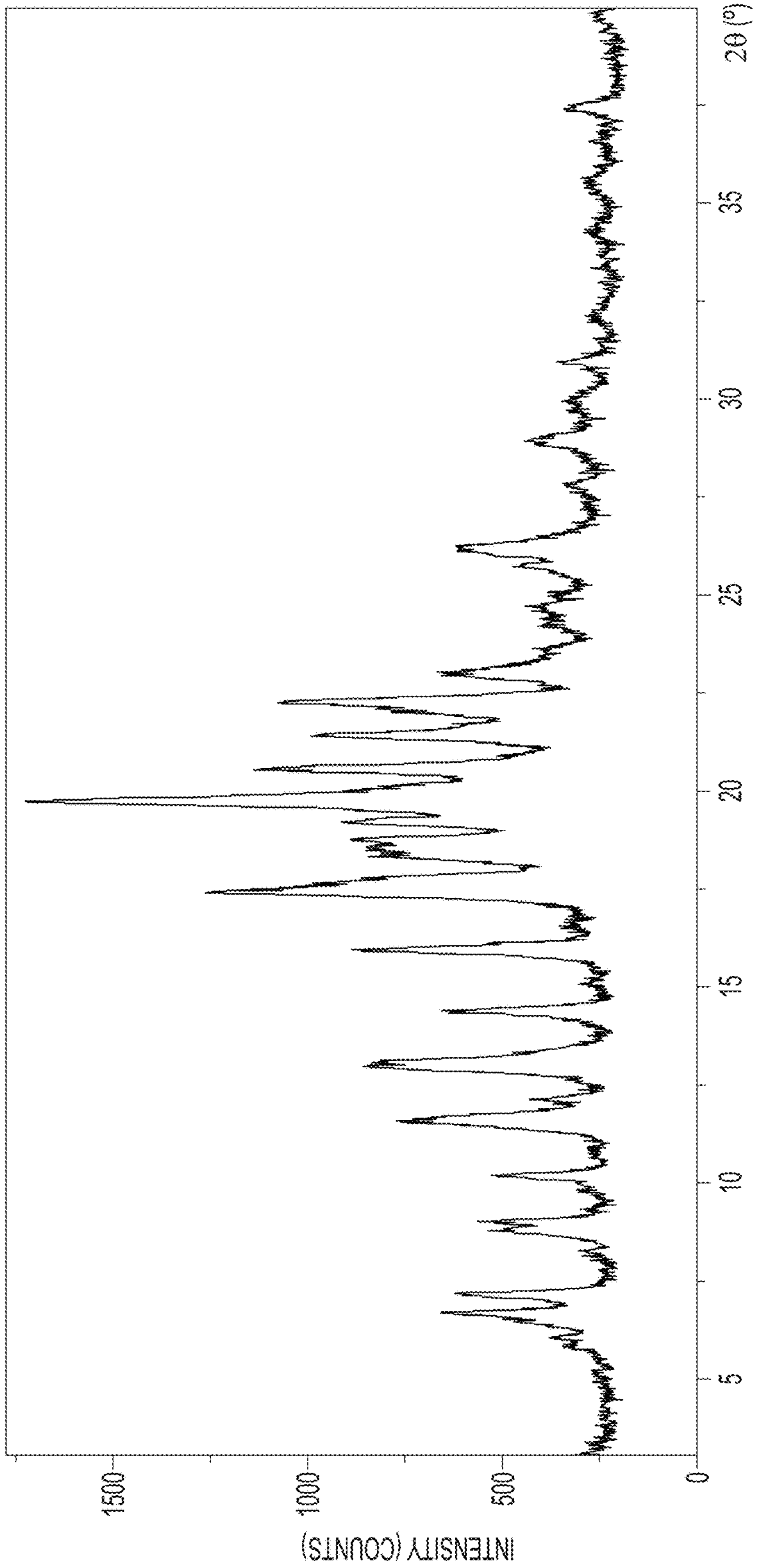
FIG. 7 is an X-ray powder diffraction (XRPD) pattern of the mesylate crystal form G of the compound represented by formula (I).
Figure 8:
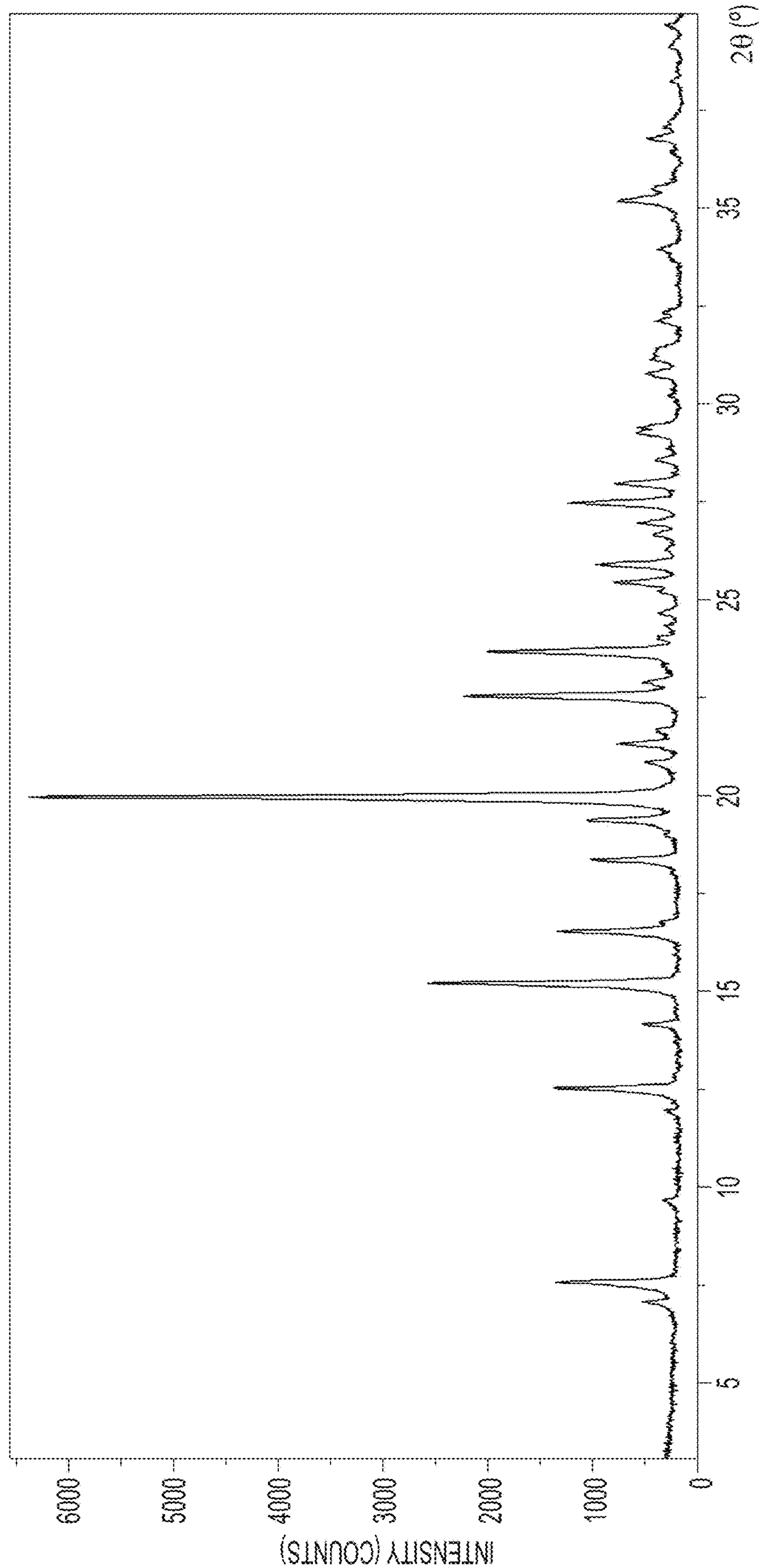
FIG. 8 is an X-ray powder diffraction (XRPD) pattern of the hydrochloride crystal form A of the compound represented by formula (I).
Figure 9:
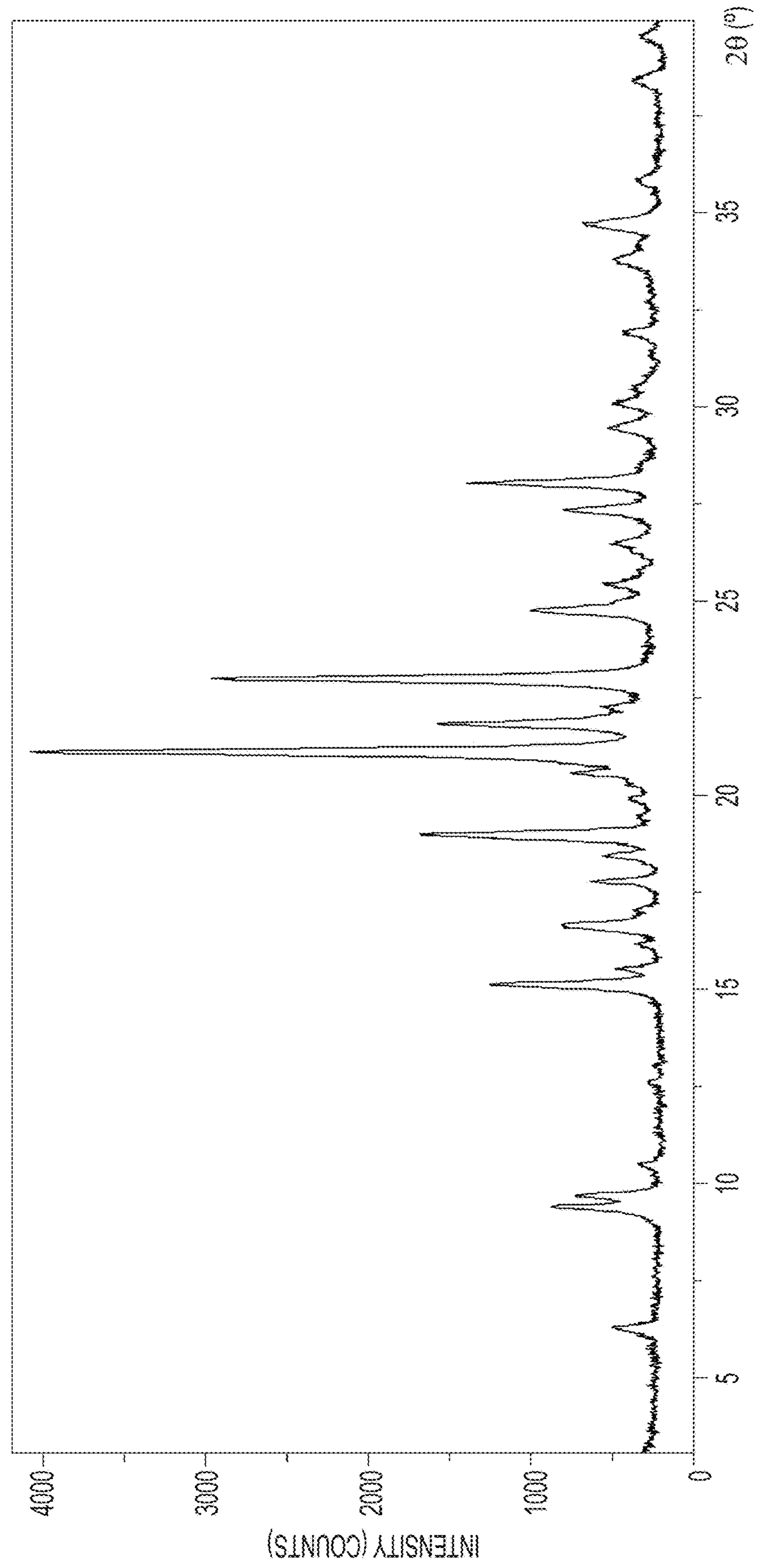
FIG. 9 is an X-ray powder diffraction (XRPD) pattern of the maleate crystal form A of the compound represented by formula (I).
Figure 10:
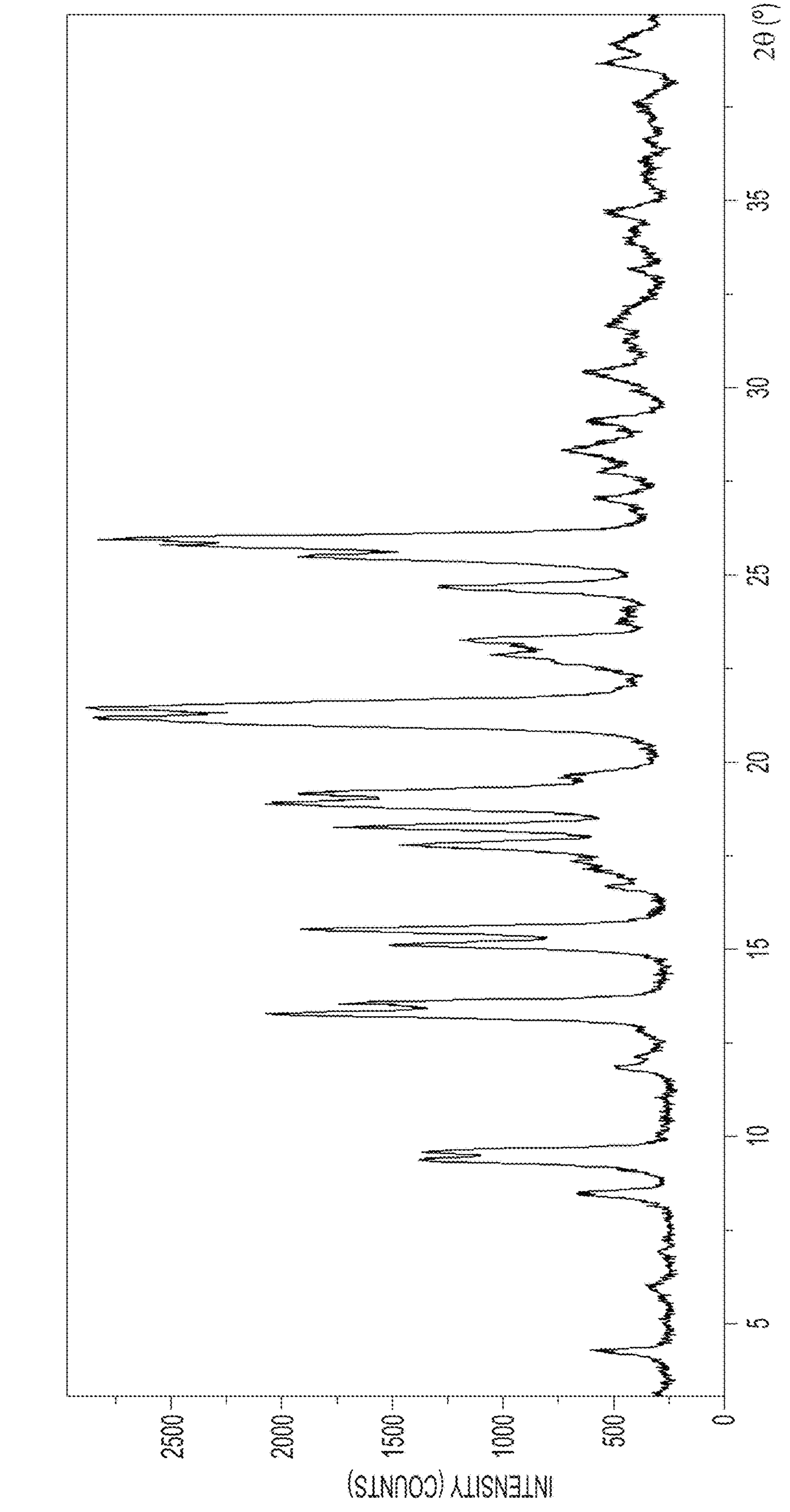
FIG. 10 is an X-ray powder diffraction (XRPD) pattern of the p-toluenesulfonate crystal form A of the compound represented by formula (I).
Figure 11:
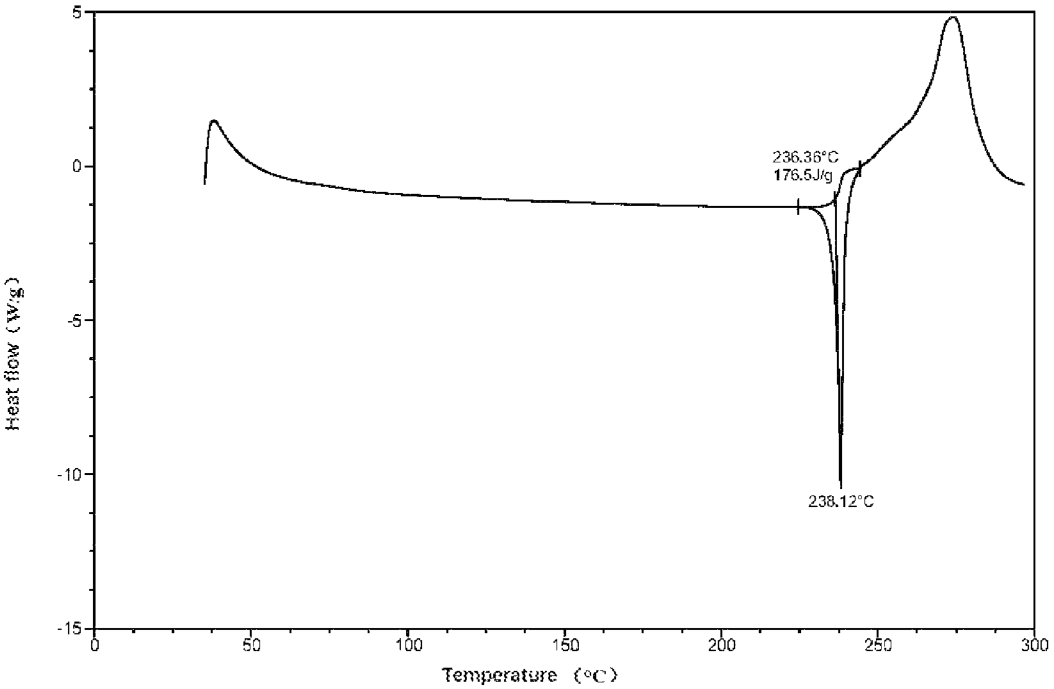
FIG. 11 is a differential scanning calorimetry (DSC) diagram of the mesylate crystal form A of the compound represented by formula (I).

3. The salt of claim 1, wherein the mesylate is mesylate crystal form B, and the mesylate crystal form B has an X-ray powder diffraction pattern substantially as shown in FIG. 2.

4. The salt of claim 1, wherein the mesylate is mesylate crystal form B, the differential scanning calorimetry diagram of the mesylate crystal form B comprises an endothermic peak at 230.55° C.±3° C.

Figure 12:
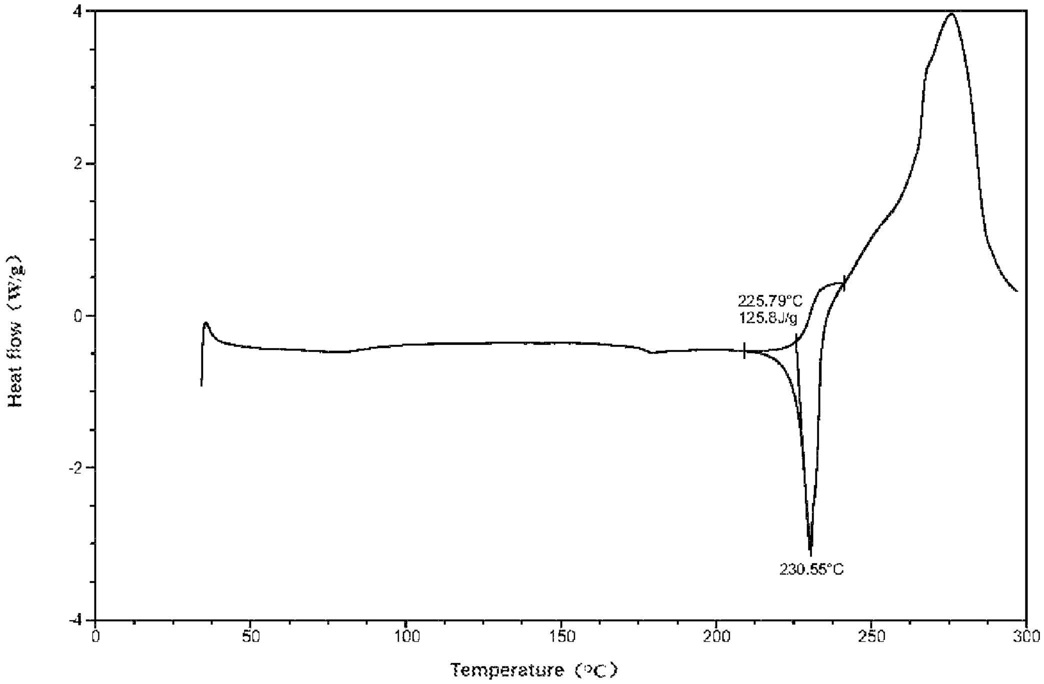
FIG. 12 is a differential scanning calorimetry (DSC) diagram of the mesylate crystal form B of the compound represented by formula (I).
Figure 13:
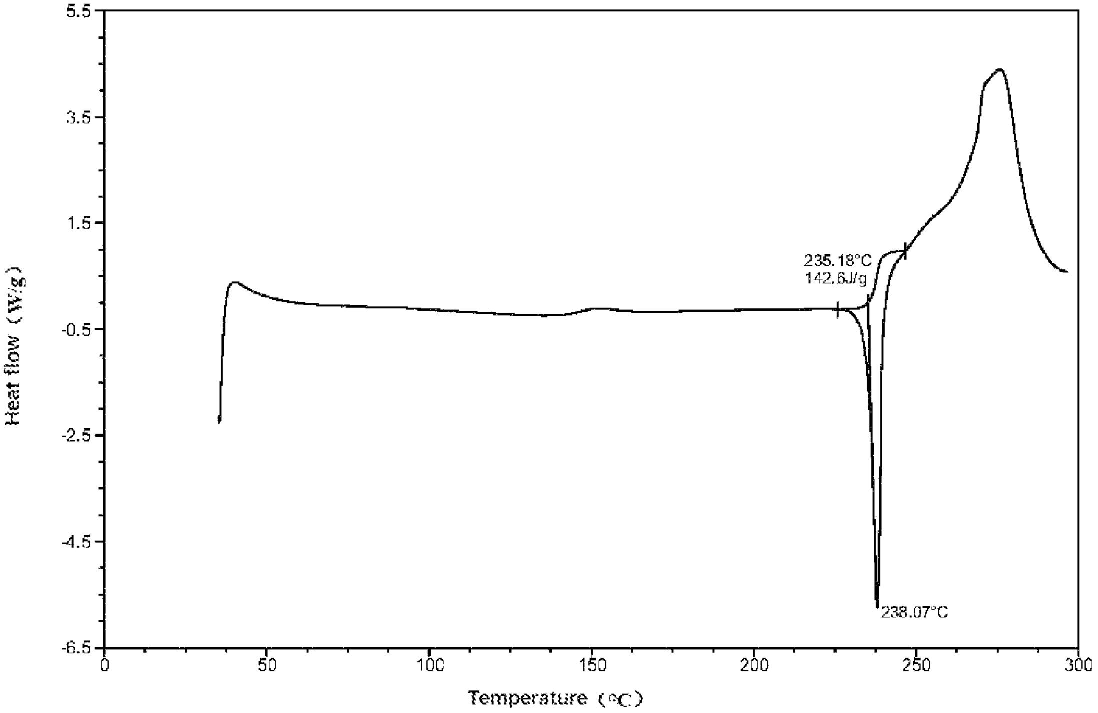
FIG. 13 is a differential scanning calorimetry (DSC) diagram of the mesylate crystal form E of the compound represented by formula (I).
Figure 14:
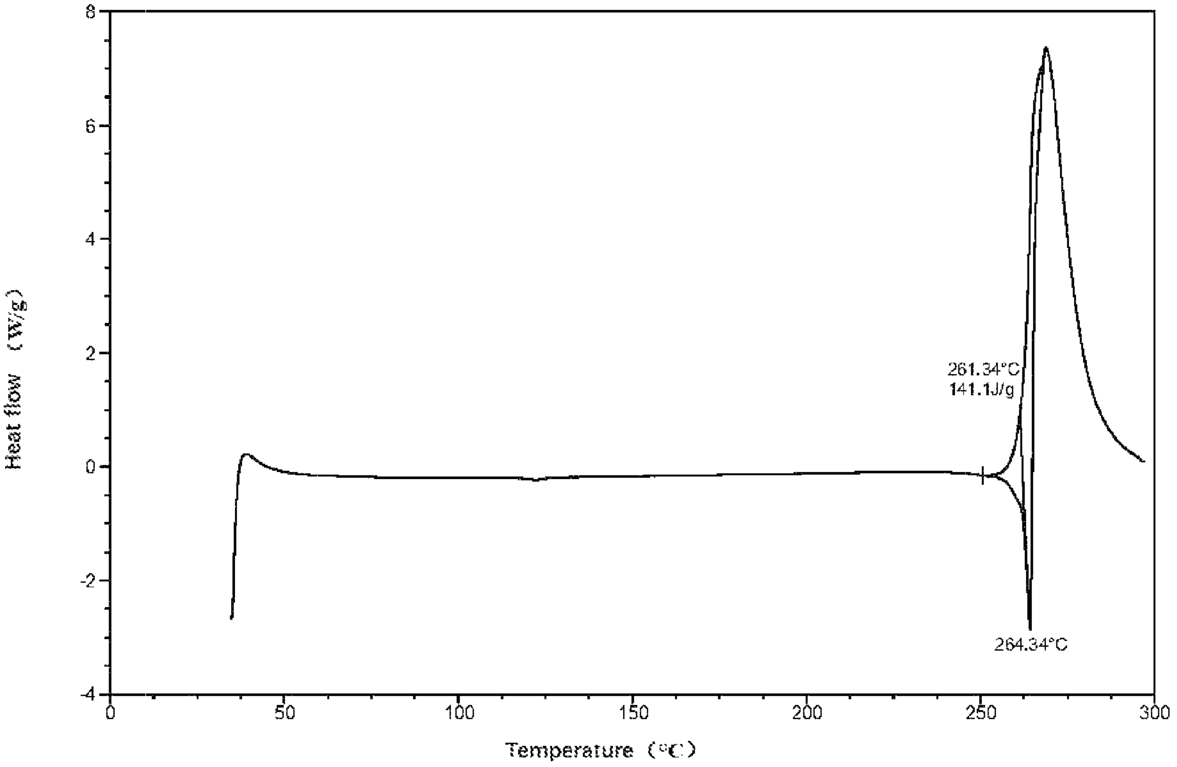
FIG. 14 is a differential scanning calorimetry (DSC) diagram of the hydrochloride crystal form A of the compound represented by formula (I).
Figure 15:
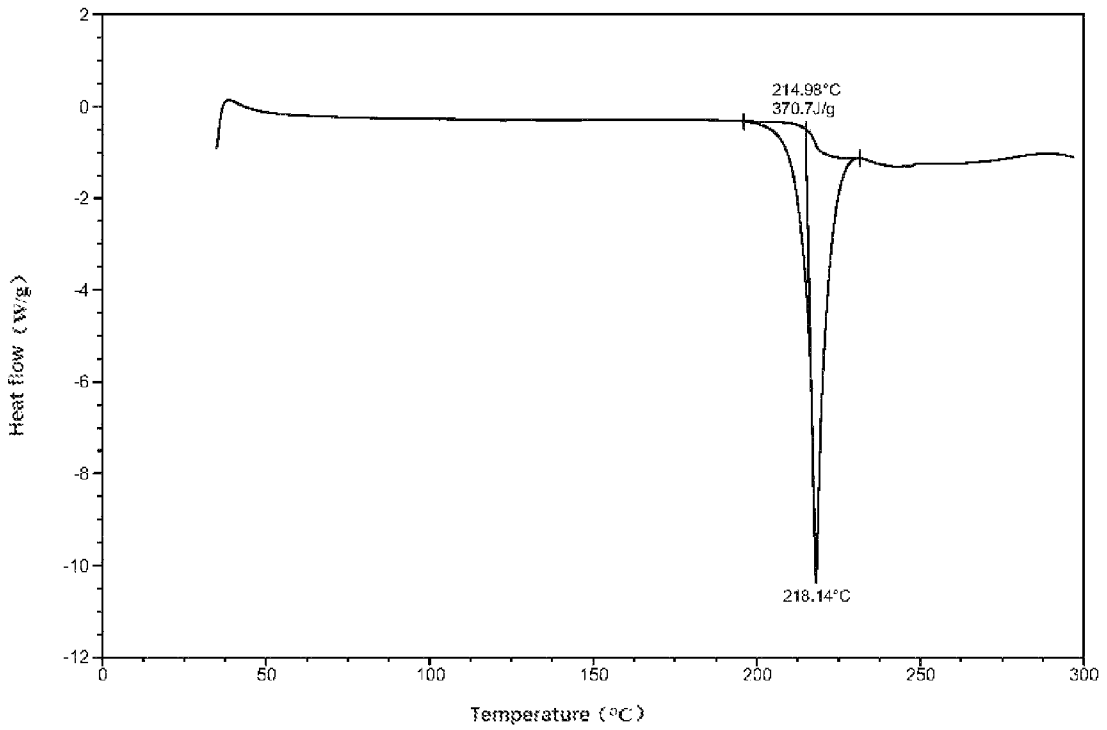
FIG. 15 is a differential scanning calorimetry (DSC) diagram of the maleate crystal form A of the compound represented by formula (I).
Figure 16:
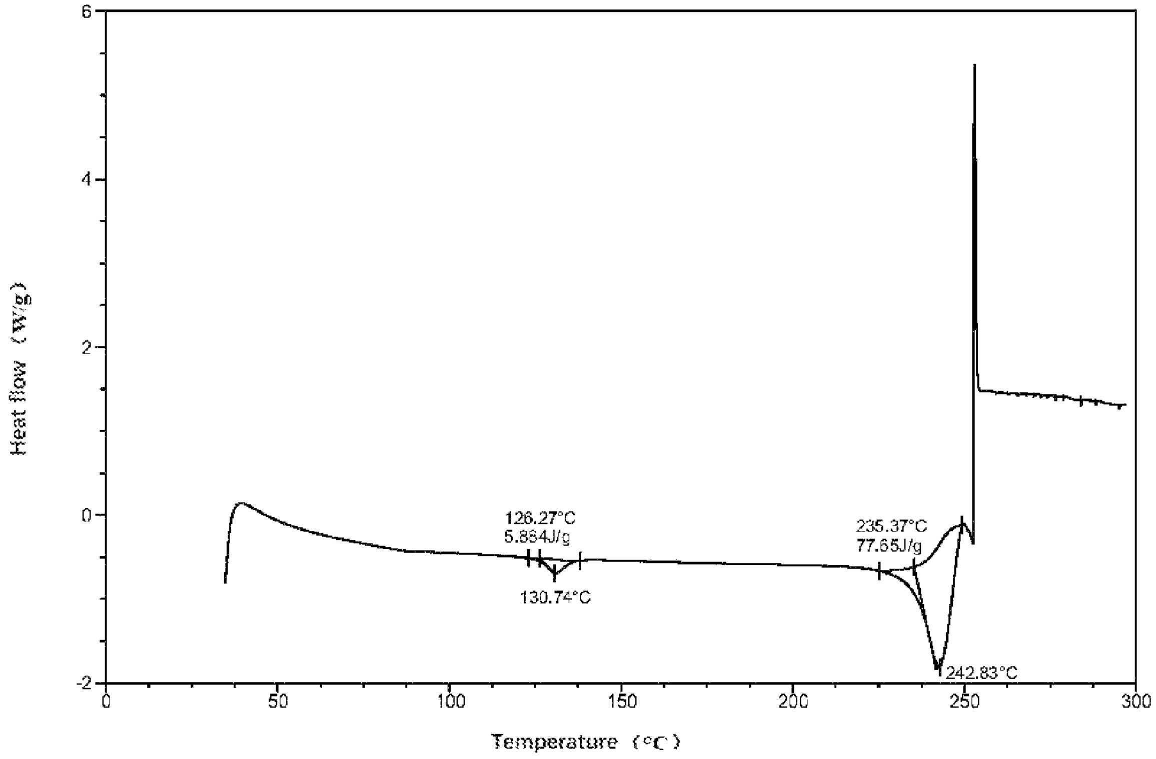
FIG. 16 is a differential scanning calorimetry (DSC) diagram of the p-toluenesulfonate crystal form A of the compound represented by formula (I).

5. The salt of claim 1, wherein the mesylate is mesylate crystal form B, and the mesylate crystal form B has a differential scanning calorimetry diagram substantially as shown in FIG. 12.

6. A pharmaceutical composition comprising the salt of claim 1, and a pharmaceutically acceptable carrier, excipient, diluent, adjuvant or a combination thereof.

7. A method of treating or alleviating diseases regulated by MAO-B in a subject, comprising administering to the subject a therapeutically effective amount of the salt of claim 1.

8. The method of claim 7, wherein the disease regulated by MAO-B is a neurodegenerative disease, psychosis or cancer;

wherein, the neurodegenerative disease is Parkinson's disease, cerebral ischemia, Alzheimer's disease, amyotrophic lateral sclerosis, bovine spongiform encephalopathy, Huntington's disease, Creutzfeldt-Jakob disease, ataxia-telangiectasia, cerebellar atrophy, spinal muscular atrophy, primary lateral sclerosis, or multiple sclerosis.

9. A method of treating or alleviating diseases regulated by MAO-B in a subject, comprising administering to the subject a therapeutically effective amount of the pharmaceutical composition of claim 6.

10. The method of claim 9, wherein the disease regulated by MAO-B is a neurodegenerative disease, psychosis or cancer;

wherein, the neurodegenerative disease is Parkinson's disease, cerebral ischemia, Alzheimer's disease, amyotrophic lateral sclerosis, bovine spongiform encephalopathy, Huntington's disease, Creutzfeldt-Jakob disease, ataxia-telangiectasia, cerebellar atrophy, spinal muscular atrophy, primary lateral sclerosis, or multiple sclerosis.

* * * * *